(12) United States Patent
Bourne

(10) Patent No.: US 10,034,953 B2
(45) Date of Patent: Jul. 31, 2018

(54) MODULAR AIR FRESHENER SYSTEM

(71) Applicant: ENERGIZER BRANDS II, LLC, St. Louis, MO (US)

(72) Inventor: Christopher Bourne, Draper, UT (US)

(73) Assignee: ENERGIZER BRANDS II, LLC, St. Louis, MO (US)

( * ) Notice: Subject to any disclaimer, the term of this patent is extended or adjusted under 35 U.S.C. 154(b) by 42 days.

(21) Appl. No.: 15/334,740

(22) Filed: Oct. 26, 2016

(65) Prior Publication Data
US 2017/0112955 A1 Apr. 27, 2017

Related U.S. Application Data

(60) Provisional application No. 62/246,370, filed on Oct. 26, 2015.

(51) Int. Cl.
*B01F 3/04* (2006.01)
*A61L 9/12* (2006.01)
*A61L 9/03* (2006.01)
*B60H 3/00* (2006.01)

(52) U.S. Cl.
CPC .............. *A61L 9/122* (2013.01); *A61L 9/032* (2013.01); *A61L 9/125* (2013.01); *B01F 3/04085* (2013.01); *B60H 3/00* (2013.01); *A61L 2209/131* (2013.01); *A61L 2209/133* (2013.01); *A61L 2209/135* (2013.01); *A61L 2209/15* (2013.01)

(58) Field of Classification Search
CPC ................ B01F 3/04; B01F 3/04085

USPC ............... 261/94, DIG. 88, DIG. 89; 239/47; 422/124
See application file for complete search history.

(56) References Cited

U.S. PATENT DOCUMENTS

| | | | |
|---|---|---|---|
| 4,197,271 | A | 4/1980 | Fenstermaker et al. |
| 4,258,004 | A | 3/1981 | Valenzona et al. |
| 4,604,245 | A * | 8/1986 | Gutierrez ............... A61L 9/122 239/59 |
| 4,968,456 | A * | 11/1990 | Muderlak ............... A61L 9/122 137/60 |
| 5,269,723 | A | 12/1993 | Bender |
| 5,788,931 | A | 8/1998 | Munoz Quintana |
| 5,833,929 | A | 11/1998 | Watson et al. |
| 5,932,147 | A | 8/1999 | Chen |
| 6,099,137 | A | 8/2000 | McCormack et al. |
| 6,103,201 | A | 8/2000 | Green |
| 6,123,906 | A | 9/2000 | Farmer |
| 6,416,043 | B1 | 7/2002 | Eisenbraun |
| 8,197,761 | B1 | 6/2012 | Miller-Larry |
| 8,662,480 | B1 | 3/2014 | Irvin |
| 8,673,223 | B1 | 3/2014 | Finlay |

(Continued)

FOREIGN PATENT DOCUMENTS

WO WO 2009/003704 A2 1/2009

*Primary Examiner* — Robert A Hopkins
(74) *Attorney, Agent, or Firm* — Alston & Bird LLP

(57) ABSTRACT

Example embodiments provide a modular air freshener system. The modular air freshener system comprises a plurality of different carriers and at least one scent device. The scent device is separately and removably carriable by each of the plurality of different carriers. At least one of the different carriers is carriable by another one of the plurality of different carriers. The each of the carriers may be passive, active and self-powered, or active and externally-powered.

20 Claims, 28 Drawing Sheets

(56) References Cited

U.S. PATENT DOCUMENTS

| | | | |
|---|---|---|---|
| 9,042,712 | B2 | 5/2015 | Irvin et al. |
| 2002/0176704 | A1 | 11/2002 | Roe |
| 2002/0197189 | A1 | 12/2002 | Lua |
| 2007/0057084 | A1 | 3/2007 | Vieira |
| 2010/0243754 | A1 | 9/2010 | Harris |

* cited by examiner

MODULAR AIR FRESHENER SYSTEM

CROSS-REFERENCE TO RELATED APPLICATIONS

This application claims priority of U.S. Provisional Application No. 62/246,370, filed Oct. 26, 2015, the contents of which are hereby incorporated in reference herein in their entireties.

BACKGROUND OF THE DISCLOSURE

Field of the Disclosure

The present disclosure relates generally to air fresheners.

Related Art

Various different types of air fresheners have been developed, particularly for use in vehicles. Vent stick type air fresheners include an aromatic body carried by the air vent, and utilizing air flow therefrom to disperse scent from the aromatic body. Cigarette lighter or power outlet type air fresheners can utilize the power outlet socket of the vehicle to power a heat source to help disperse scent.

SUMMARY OF THE DISCLOSURE

Example embodiments provide an air freshener that can support multiple different uses, for example including the air vent, the power outlet, and the visor of a vehicle. In addition, example embodiments provide a modular air freshener with interchangeable components.

The disclosure provides a modular air freshener system comprising a plurality of different carriers. At least one scent device is separately and removably carriable by each of the plurality of different carriers. At least one of the different carriers is carriable by another one of the plurality of different carriers.

According to one aspect of the present disclosure, a modular air freshener system is provided. In an example embodiment, the system comprises a plurality of carriers each having a different housing. The plurality of carriers comprises a passive diffuser carrier, a self-powered carrier, and an externally-powered carrier. The self-powered carrier comprises a first housing; a power-supply disposed in the first housing; a first open end formed in the first housing; and a first blower electrically connected to the power supply, wherein the first blower is disposed in the first housing and configured to supply a flow of air through the first open end. The externally-powered carrier comprises a second housing comprising at least one electrical terminal configured to be secured relative to an external power supply; a second open end formed in the second housing; and a second blower electrically connected to the at least one electrical terminal, wherein the second blower is configured to supply a flow of air through the second open end. The diffuser carrier comprises a diffuser body having a mating end; and a scent device disposed in and carried by the diffuser body. The mating end of the diffuser body is selectively couplable to the first open end of the first housing of the self-powered carrier to complete the first housing of the self-powered carrier, and to position the scent device in the air flow supplied by the first blower. Thus, the self-powered carrier may carry the diffuser body and the scent device. The mating end of the diffuser body is selectively couplable to the second open end of the second housing of the externally-powered carrier to complete the second housing of the externally-powered carrier and position the scent device in the air flow supplied by the second blower. Thus, the externally-powered carrier may carry the diffuser body and the scent device. The system may further comprise a mount couplable to the diffuser body when the diffuser body is not coupled to the first housing or the second housing. The mount comprising a vent clip configured to be removably attachable to an air vent.

According to another aspect of the present disclosure, a modular air freshener system is provided. In example embodiments, the system comprises a plurality of different carriers. The plurality of different carriers comprises at least one unpowered or passive carrier. The system further comprises at least one scent device separately and removably carriable by each of the plurality of different carriers. At least one of the different carriers being carriable by another one of the plurality of different carriers.

According to yet another aspect of the present disclosure, a modular air freshener system is provided. In example embodiments, the system comprises a housing; scent distributor for accelerating dispersal of scent disposed in the housing; a diffuser body removably couplable to the housing; a scent device disposed in and carried by the diffuser body and being removably couplable to the housing along with the diffuser body; and a mount couplable to the diffuser body when the diffuser body is removed from the housing. The housing, the diffuser body, the scent distributor, and the scent device define an active air freshener when the diffuser body and the scent device are coupled to the housing. Thus, the diffuser body may be carried by the housing and the scent distributor may accelerate dispersal of scent from the scent device. The diffuser body, the scent device and the mount define a passive air freshener when the diffuser body and the scent device are not coupled to the housing and the mount is coupled to the diffuser body. Thus, the diffuser body may be carried by the mount.

BRIEF DESCRIPTION OF THE SEVERAL VIEWS OF THE DRAWING(S)

Reference will now be made to the accompanying drawings, which are not necessarily drawn to scale, and wherein.

DETAILED DESCRIPTION OF EXAMPLE EMBODIMENTS

Aspects of the present disclosure now will be described more fully hereinafter with reference to the accompanying drawings, in which some, but not all embodiments of the disclosure are shown. Indeed, the disclosure may be embodied in many different forms and should not be construed as limited to the embodiments set forth herein; rather, these embodiments are provided so that this disclosure will satisfy applicable legal requirements. Like numbers refer to like elements throughout.

Definitions

The term "power outlet" or "power outlet of an automobile or vehicle" is used herein to refer to any type of power outlet (e.g., receptacle) available in an automobile or vehicle, and which is typically a 12 volt outlet configured in the style to receive a cigarette lighter or other accessory. Such a power outlet can be located in a dash or console of a vehicle. Such a power outlet can include a single bore or hole extending into the dash with one or more lateral terminals disposed in the lateral sides of the bore or hole, and a distal end terminal disposed in a bottom of the bore or hole. In some embodiments, the power outlet may be a 110 volt AC power outlet of a home, building, other structure, or within an automobile or vehicle. In an example embodiment, the power outlet may be a USB receptacle. Such a power outlet may also include an adapter inserted into the power outlet. Such a power outlet can be oriented horizontally, vertically, or at an incline.

The terms "vent" and "air vent" are used interchangeably herein to refer to an air outlet in a vehicle dashboard, vehicle console, vehicle panel, building wall, building floor, and/or the like. The air outlet can be connected by ducts to a fan or blower to displace air through the duct to the air outlet. The air outlet can have a grid of louvers therein to further direct the airflow.

The term "visor" is used herein to refer to a sun shade movably affixed in a vehicle, typically adjacent to or proximal the windscreen or window, and that can pivot and/or be displaced to block sun from the driver's or passenger's eyes. A visor is an example a generally flat and thin object (e.g., panel) to which an air freshener may be configured to be removably attachable.

The terms "top" and "bottom" and "downwardly" and "upwardly" and the like are used herein relative to the air freshener device or housing thereof being oriented upright or vertical; while it is understood that the device or housing can be oriented horizontally or at an incline during use depending on the orientation of the power outlet.

The term "scent material" and "fragrant material" are used interchangeably herein to refer broadly to a material that carries a fragrance or scent, or neutralizing agent. The material may be a solid, liquid, gel or the like.

The term "clear dome" is used herein to refer to a dome that is substantially clear or transparent, or that is at least translucent to the naked eye.

Description

Figure 1:
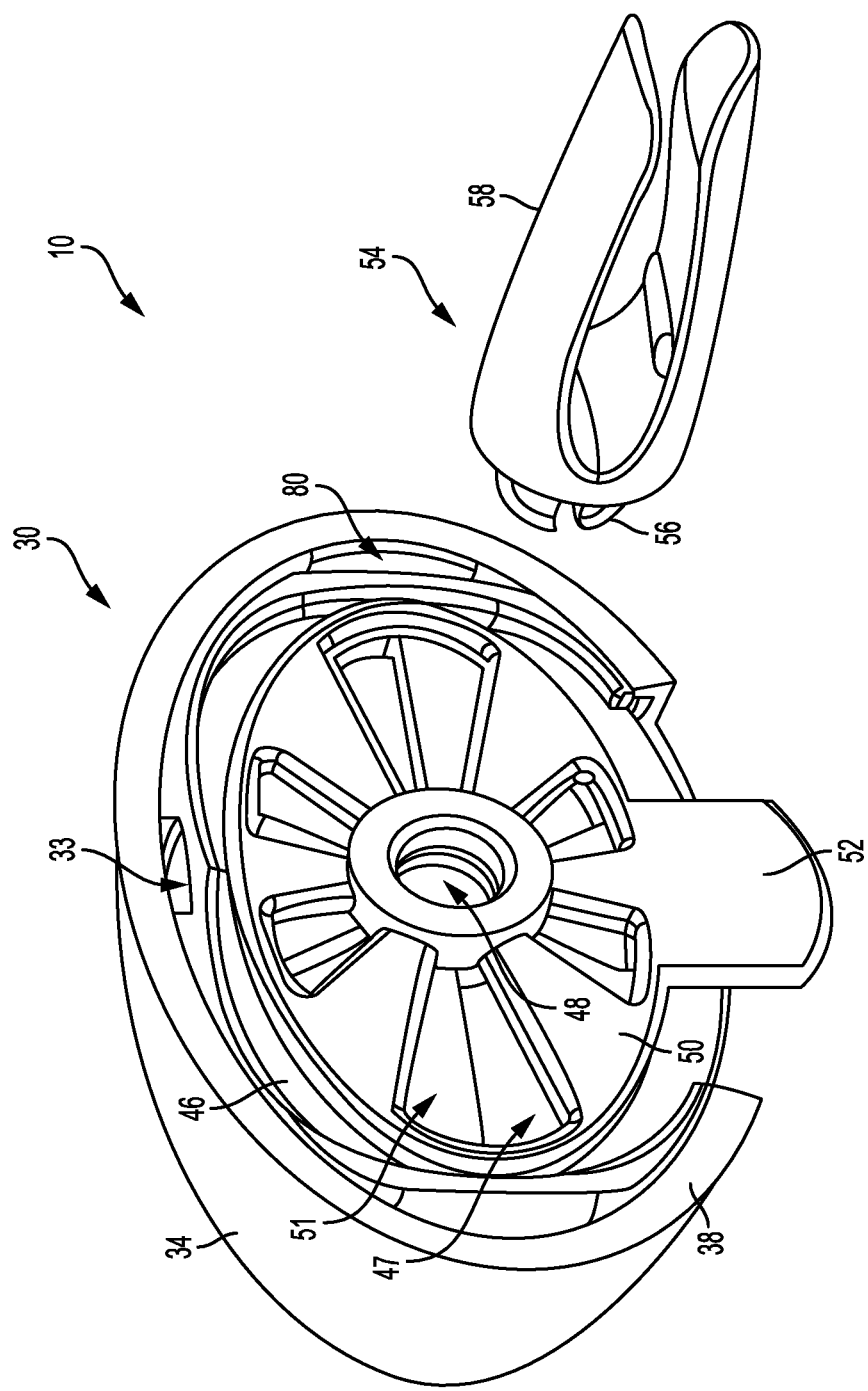
FIG. 1 is an exploded view of a diffuser air freshener, in accordance with an example embodiment.
Figure 2:
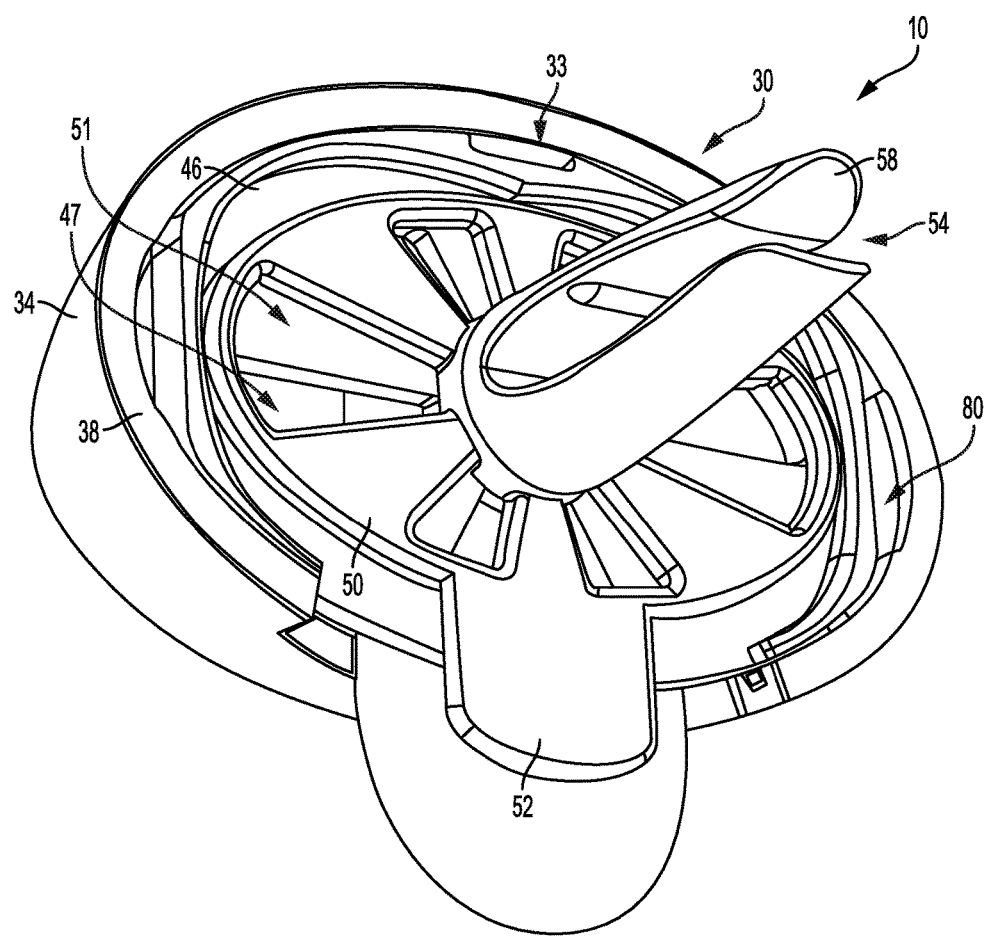
FIG. 2 is a perspective view of a diffuser, in accordance with an example embodiment.
Figure 3:
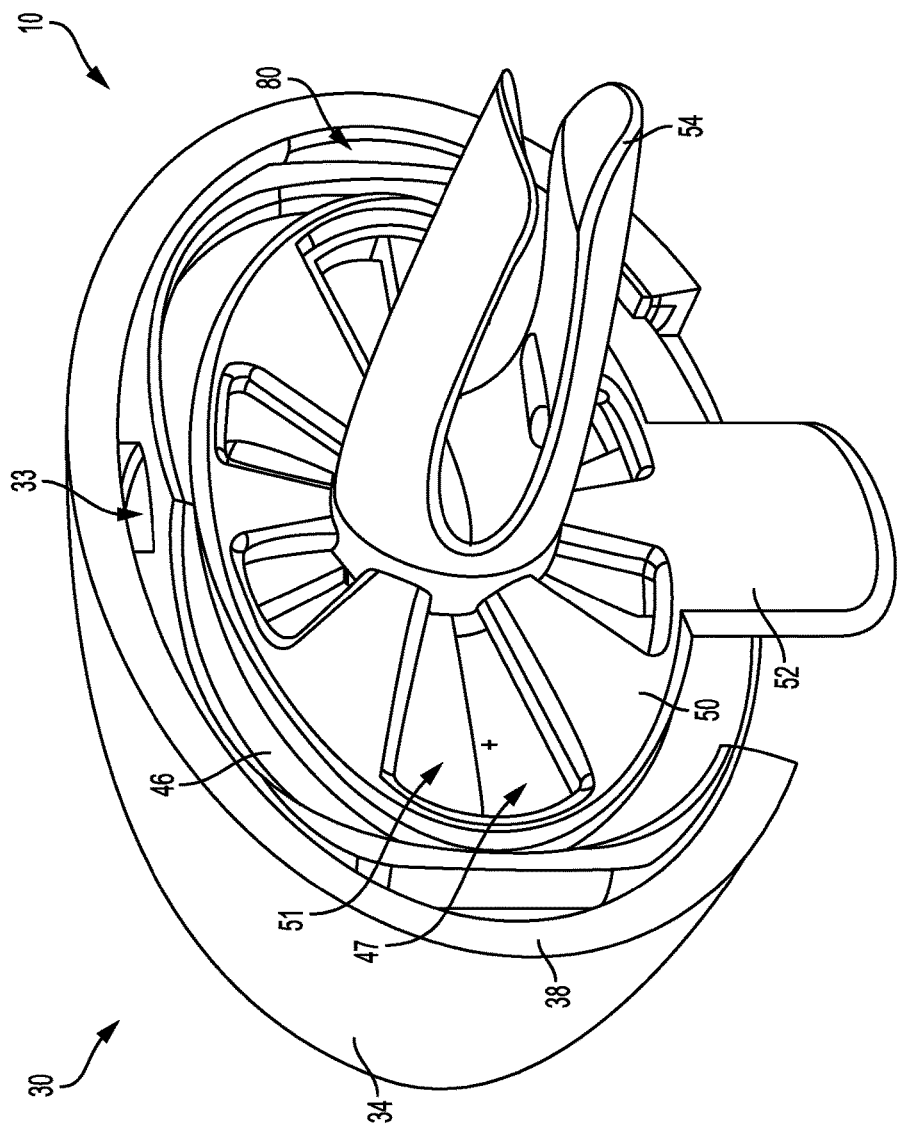
FIG. 3 is a perspective view of a diffuser, in accordance with an example embodiment.
Figure 4:
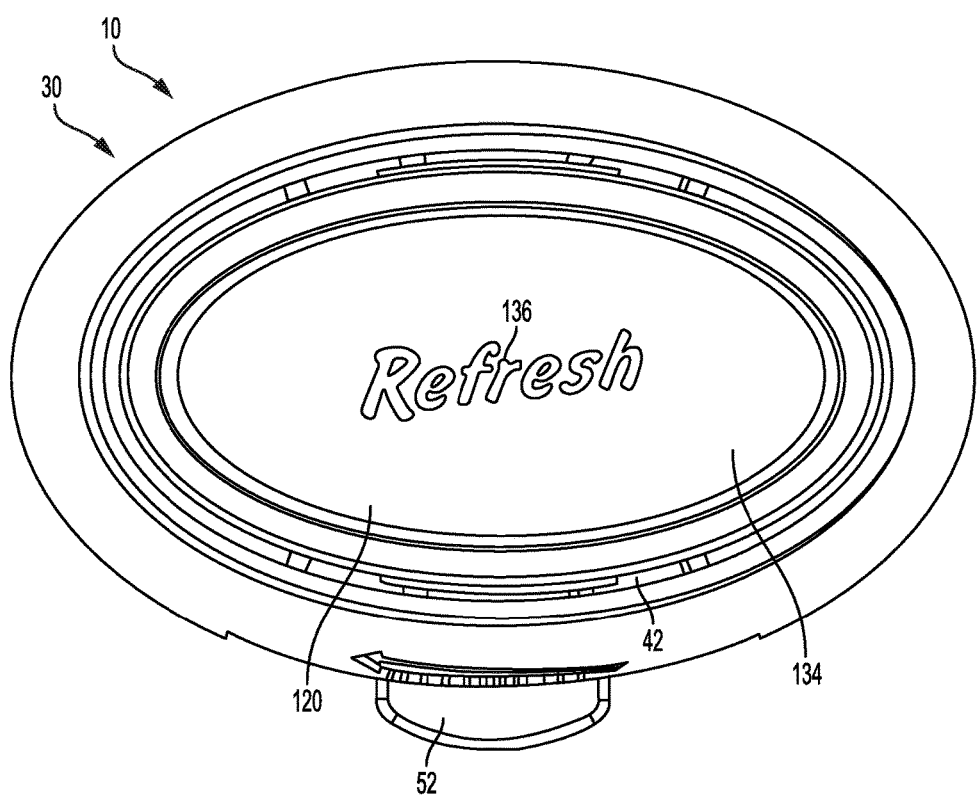
FIG. 4 is a front view of a scent device in a diffuser, in accordance with an example embodiment.
Figure 5:
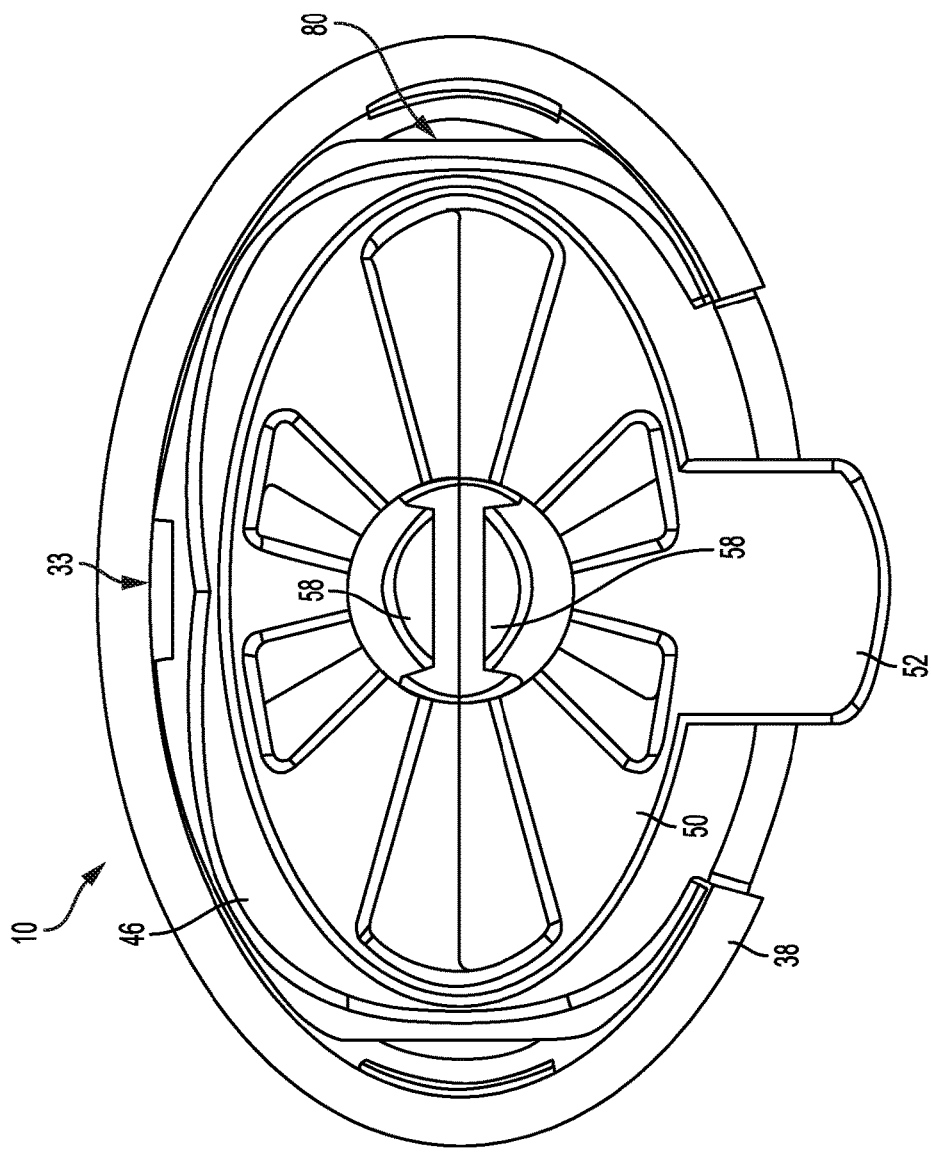
FIG. 5 is a back view of a diffuser, in accordance with an example embodiment.
Figure 7:
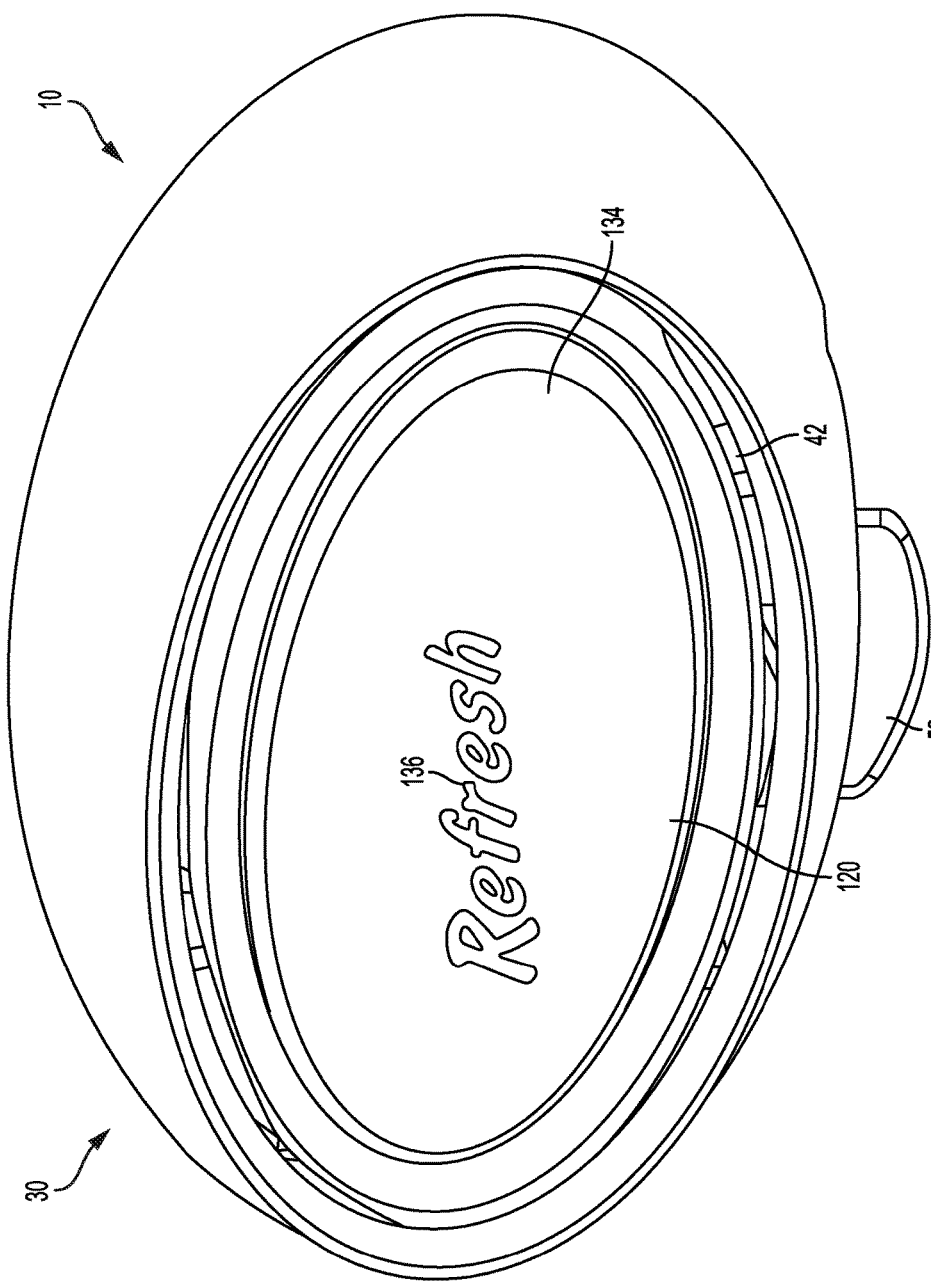
FIG. 7 is a perspective view of a scent device within a diffuser, in accordance with an example embodiment.
Figure 8:
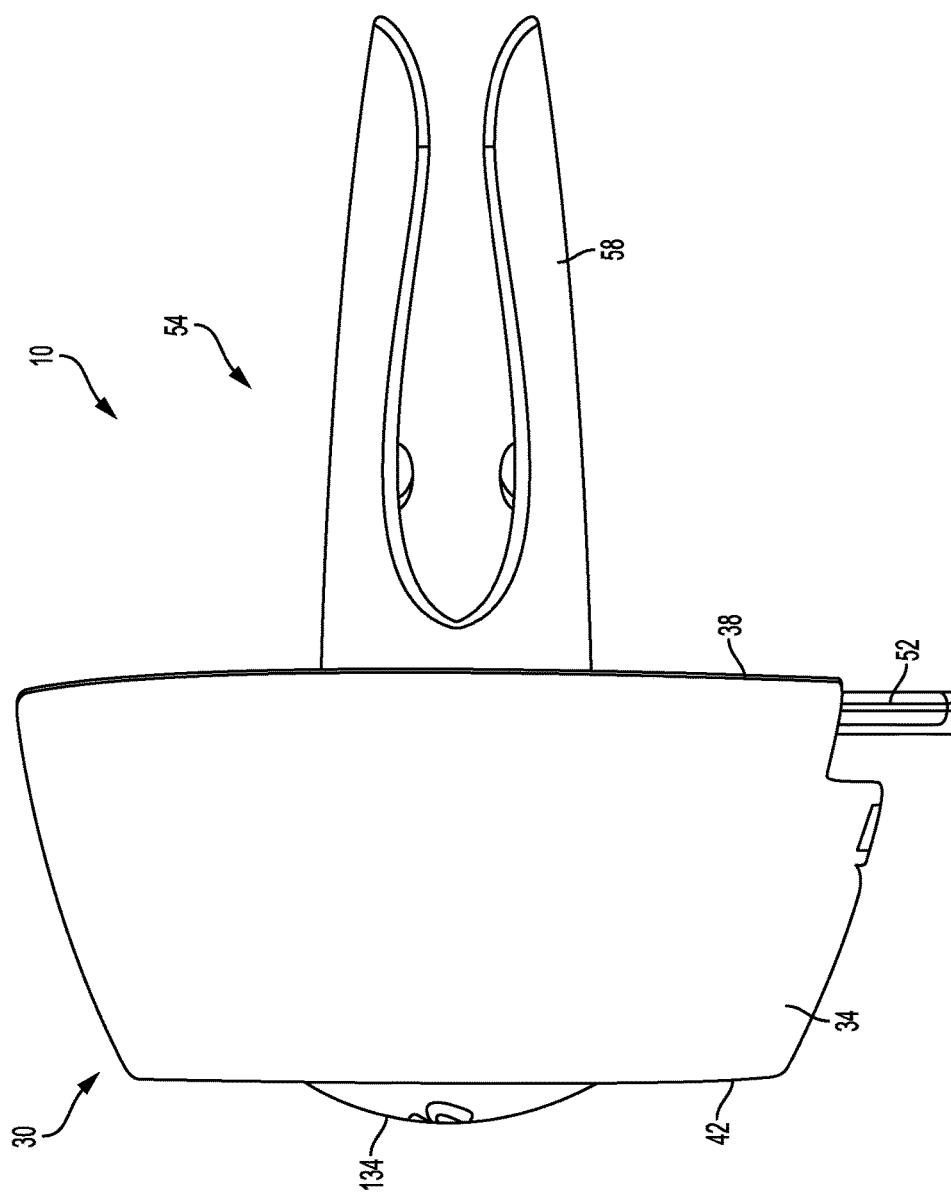
FIG. 8 is a side view of a scent device within a diffuser, in accordance with an example embodiment.
Figure 9:
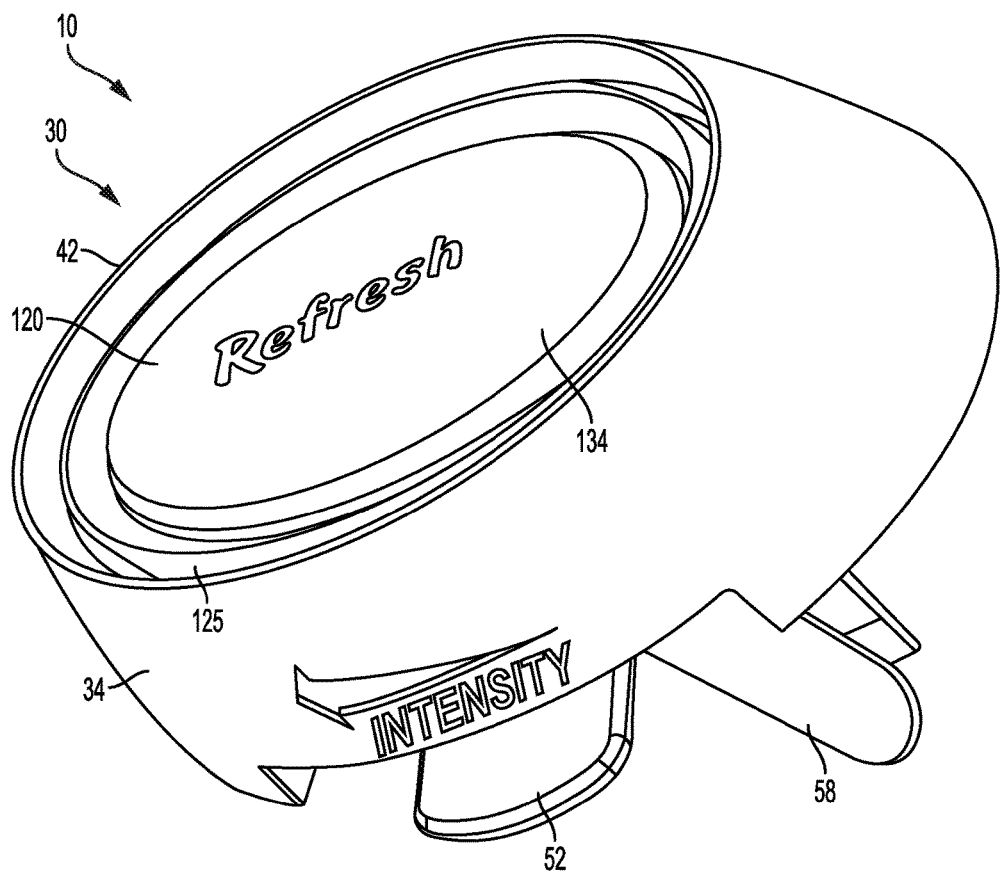
FIG. 9 is a perspective view of a scent device within a diffuser, in accordance with an example embodiment.
Figure 10:
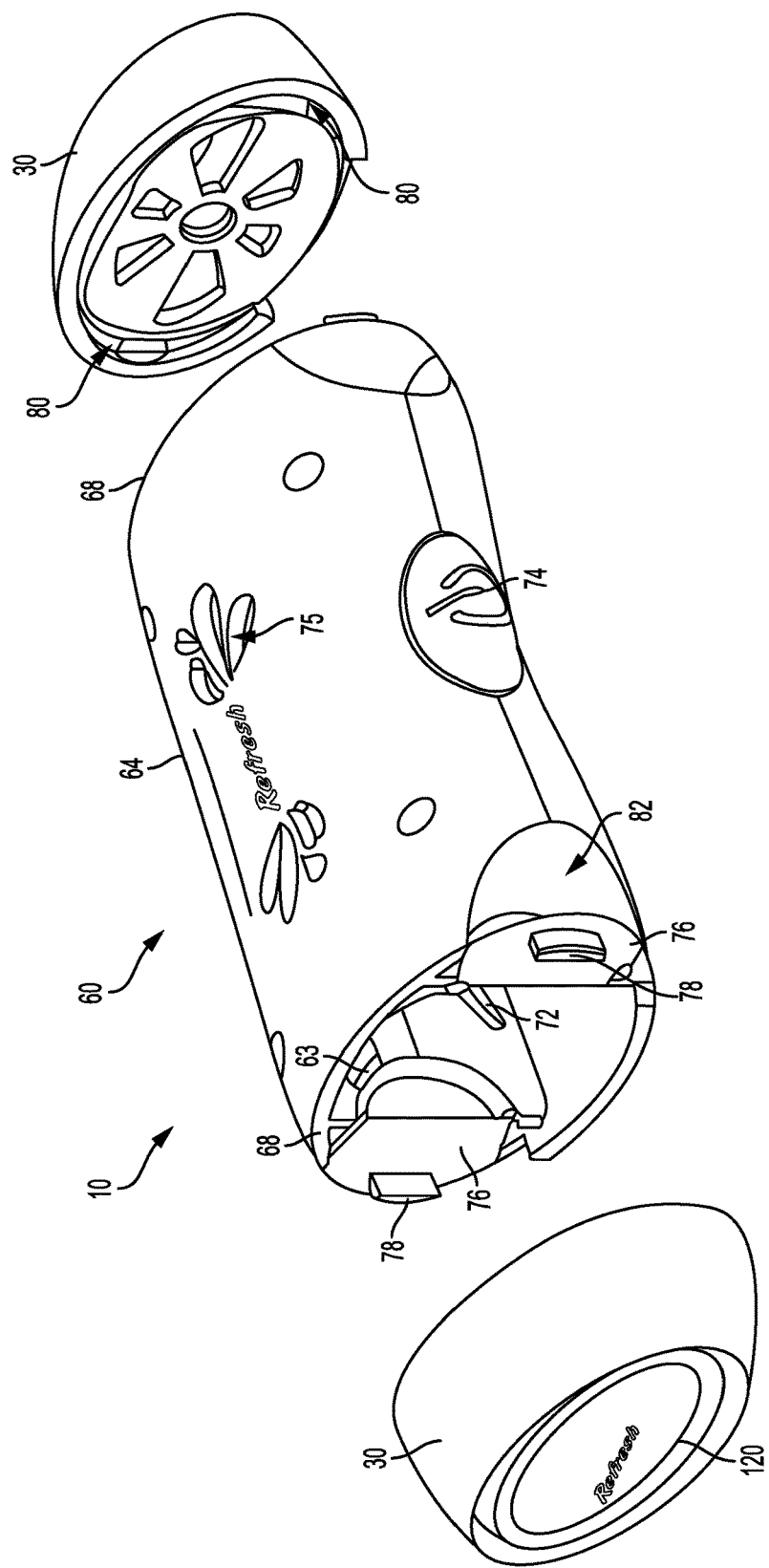
FIG. 10 is an exploded view of a panel-mount air freshener, in accordance with an example embodiment.
Figure 13:
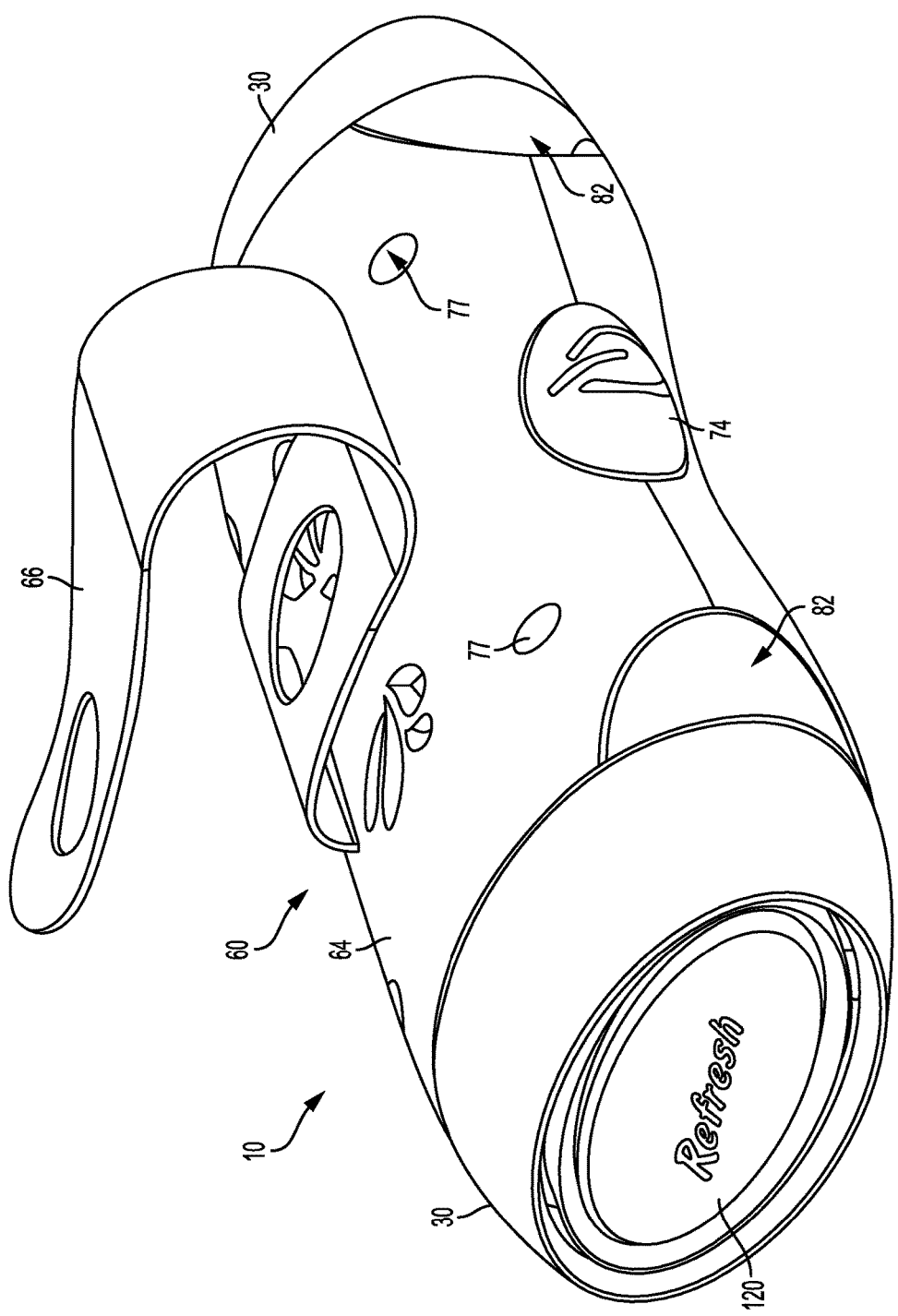
FIG. 13 is a perspective view of two diffusers having scent devices therein being carried by a panel-mount carrier, in accordance with an example embodiment.
Figure 14:
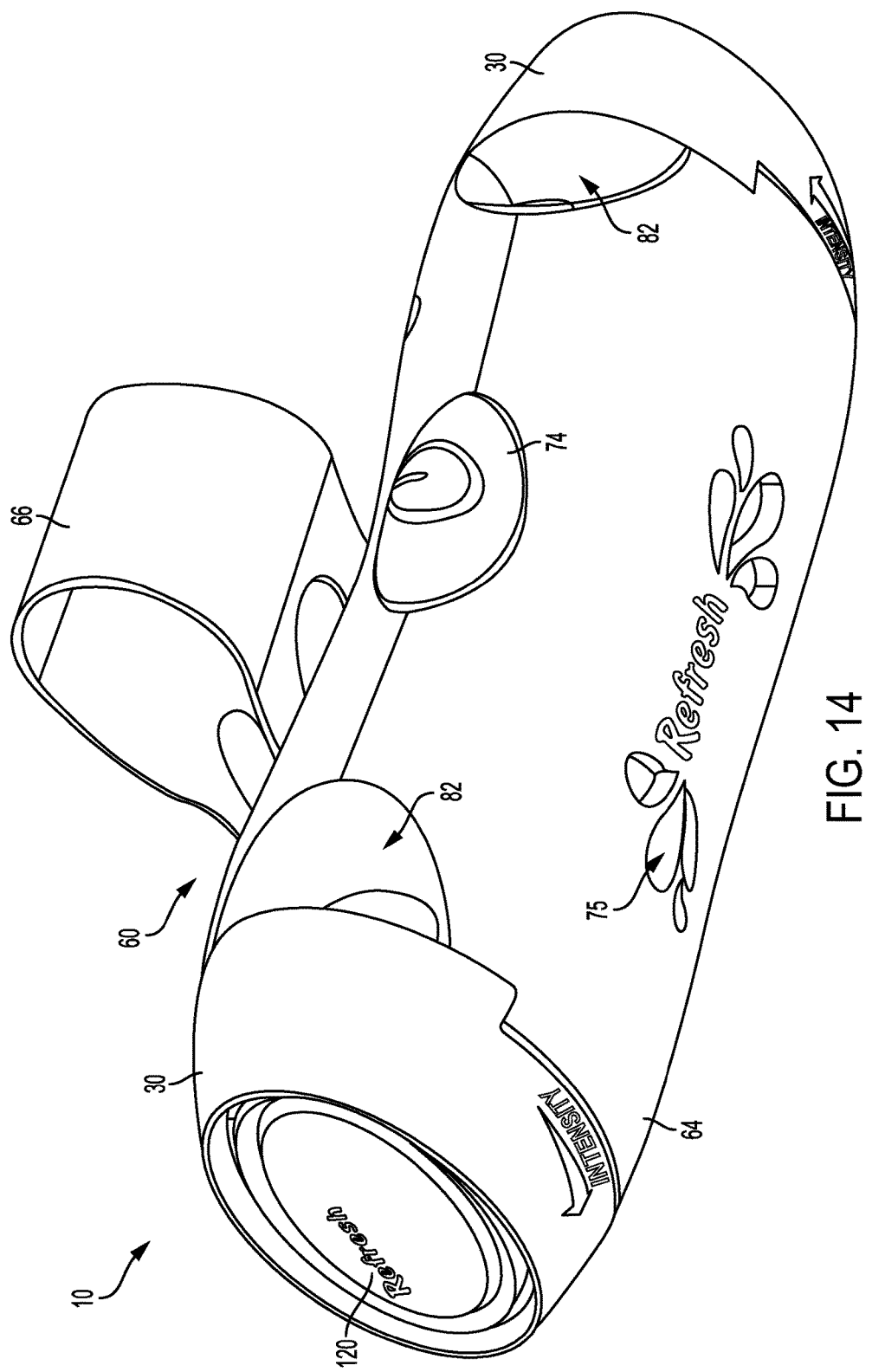
FIG. 14 is another perspective view of two diffusers having scent devices therein being carried by a panel-mount carrier, in accordance with an example embodiment.
Figure 15:
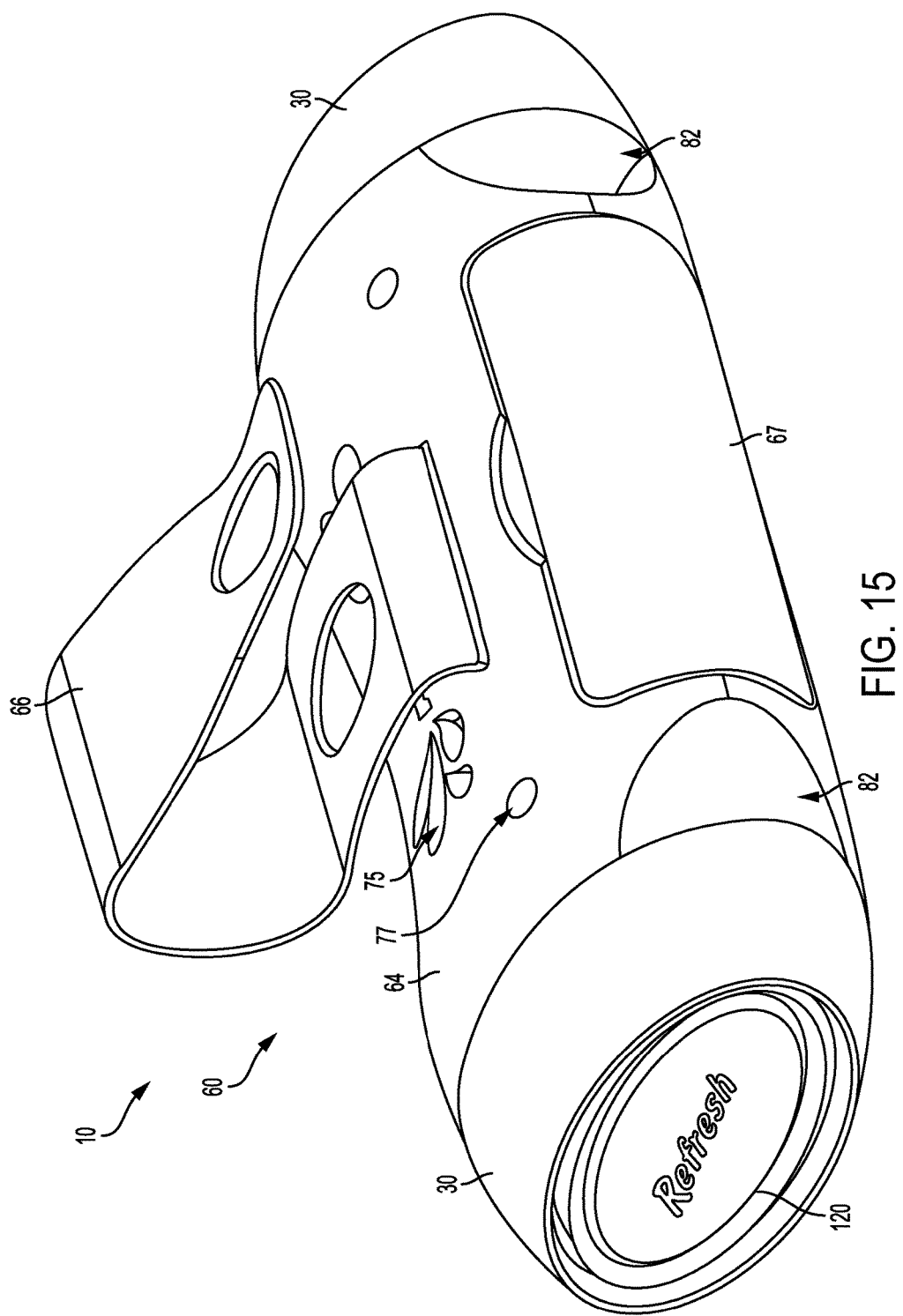
FIG. 15 is another perspective view of two diffusers having scent devices therein being carried by a panel-mount carrier, in accordance with an example embodiment.
Figure 16:
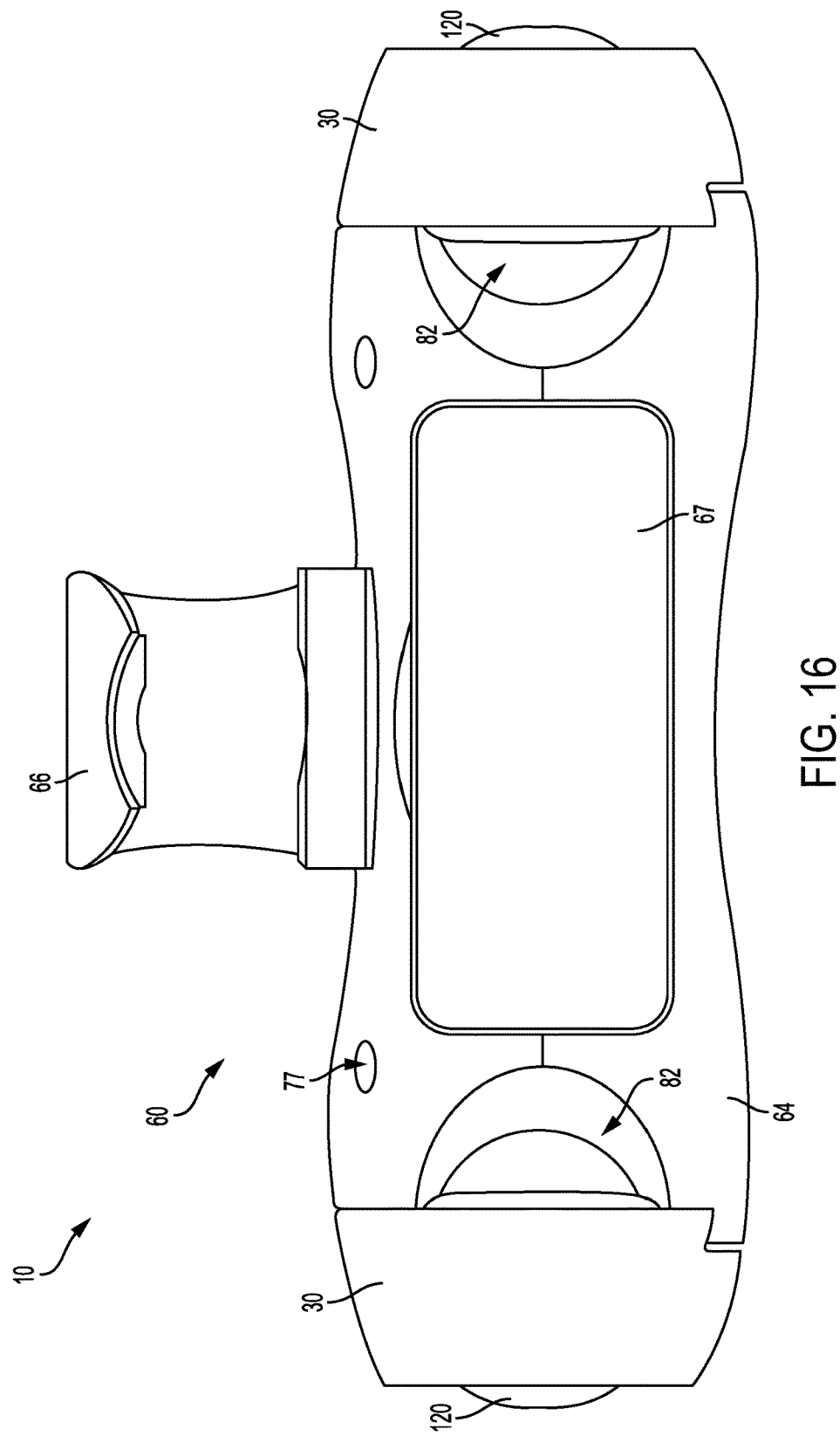
FIG. 16 is a bottom view of two diffusers having scent devices therein being carried by a panel-mount carrier, in accordance with an example embodiment.
Figure 17:
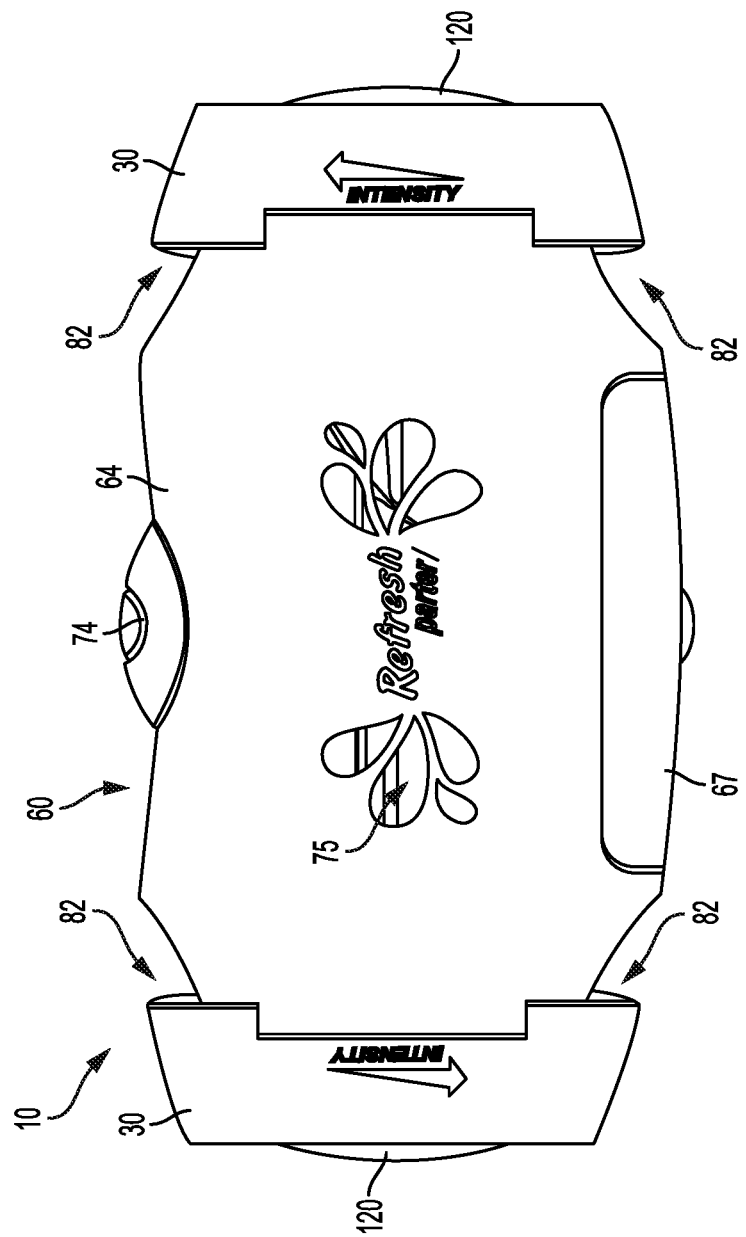
FIG. 17 is a side view of two diffusers having scent devices therein being carried by a panel-mount carrier, in accordance with an example embodiment.
Figure 18:
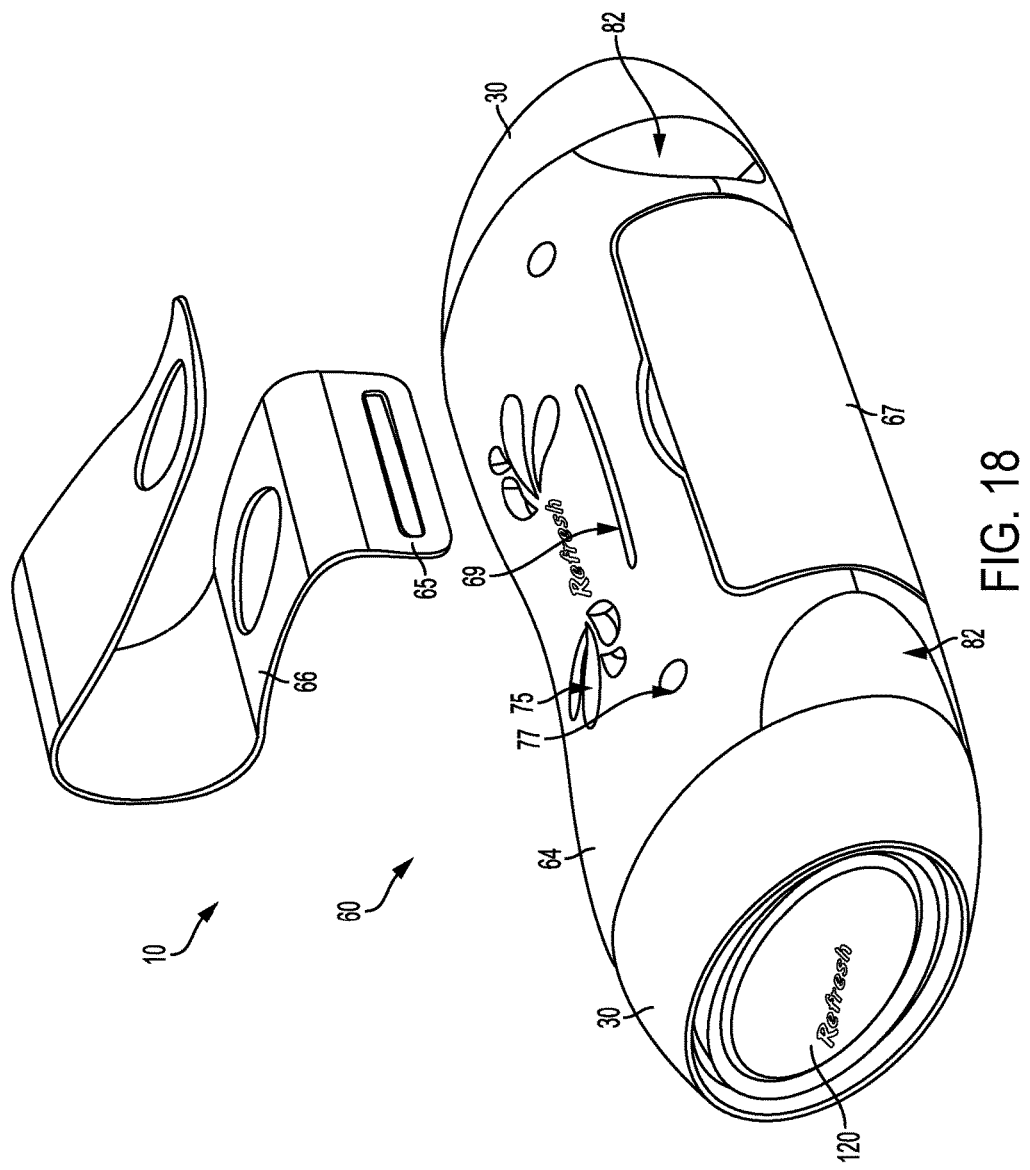
FIG. 18 is a partially exploded perspective view of two diffusers having scent devices therein being carried by a panel-mount carrier, in accordance with an example embodiment.
Figure 19:
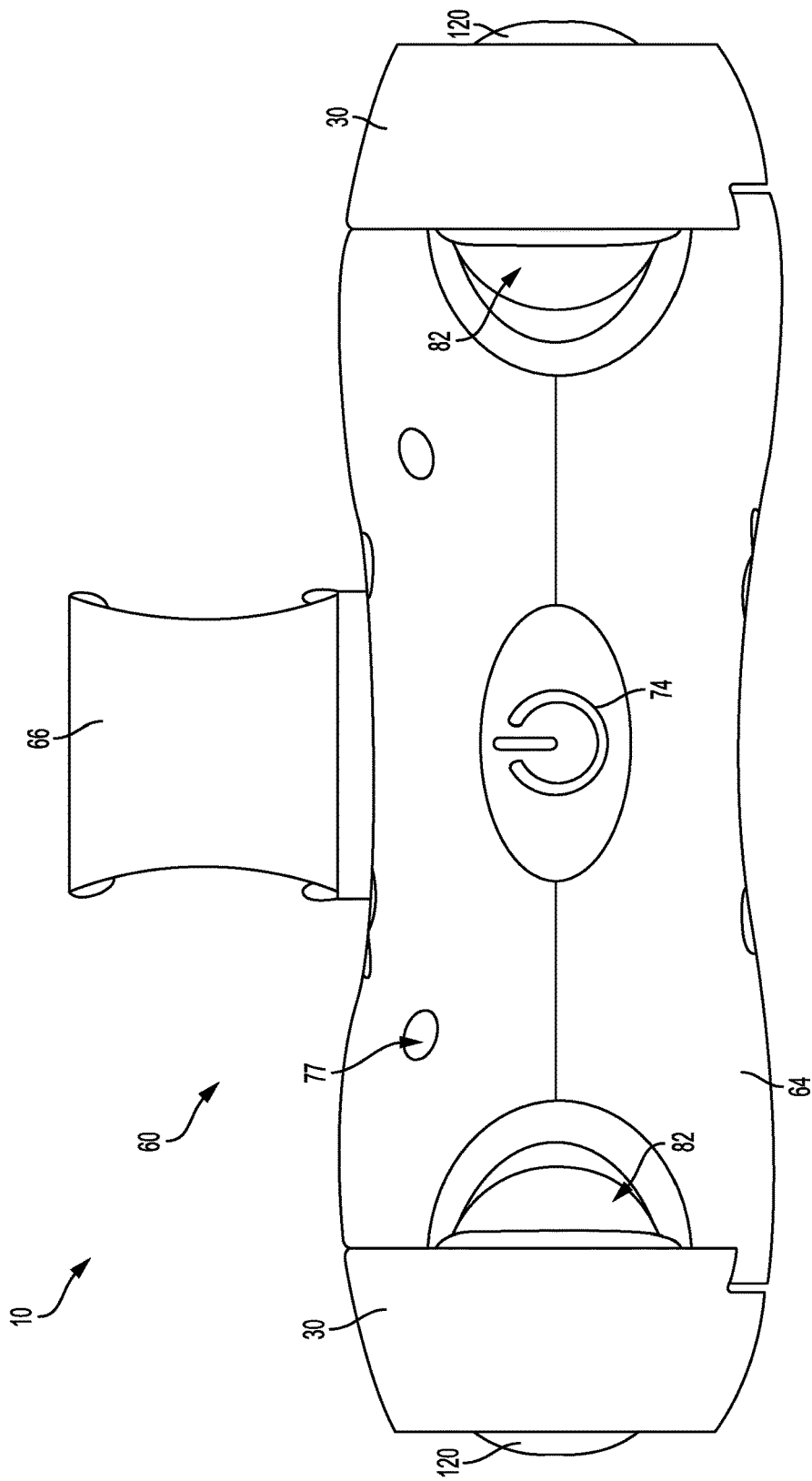
FIG. 19 is a top view of two diffusers having scent devices therein being carried by a panel-mount carrier, in accordance with an example embodiment.
Figure 20:
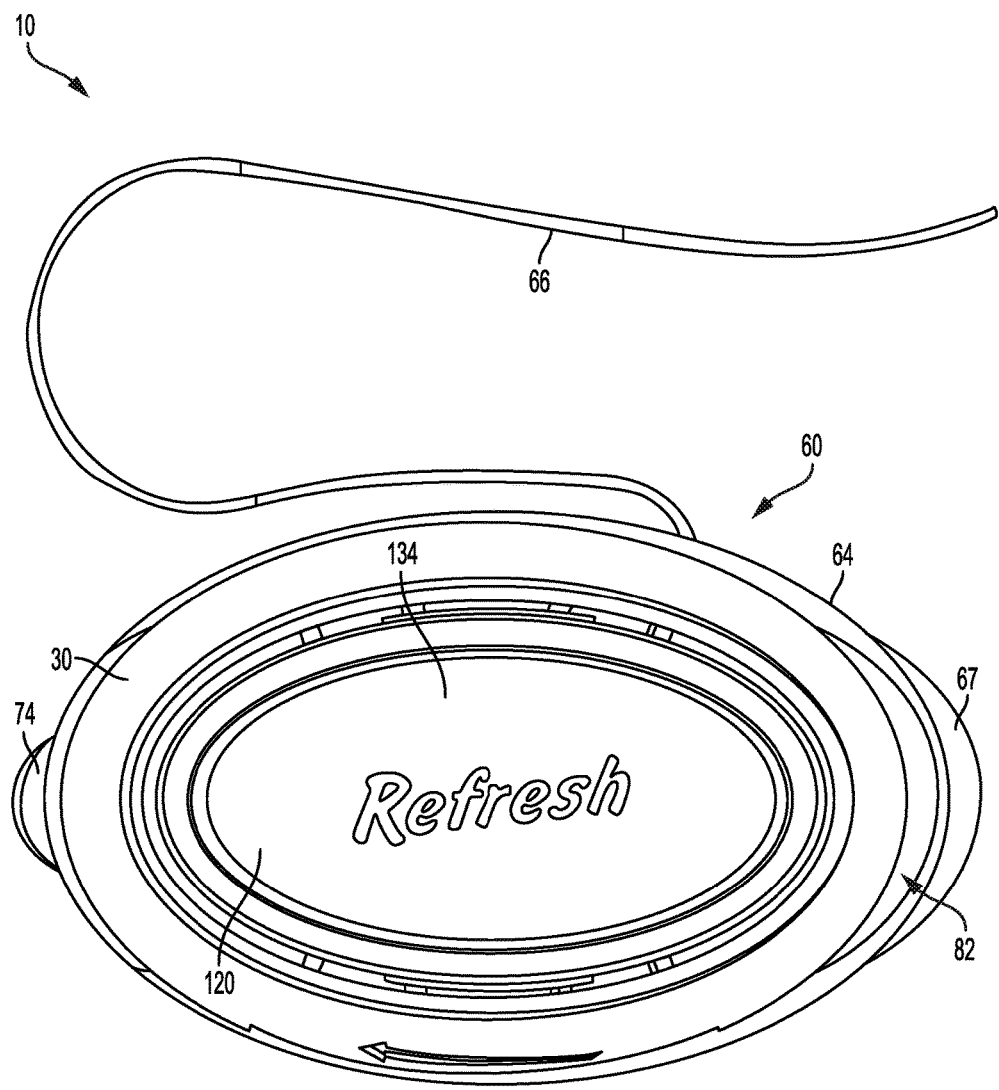
FIG. 20 is a front view of a diffuser having a scent device therein being carried by a panel-mount carrier, in accordance with an example embodiment.
Figure 21:
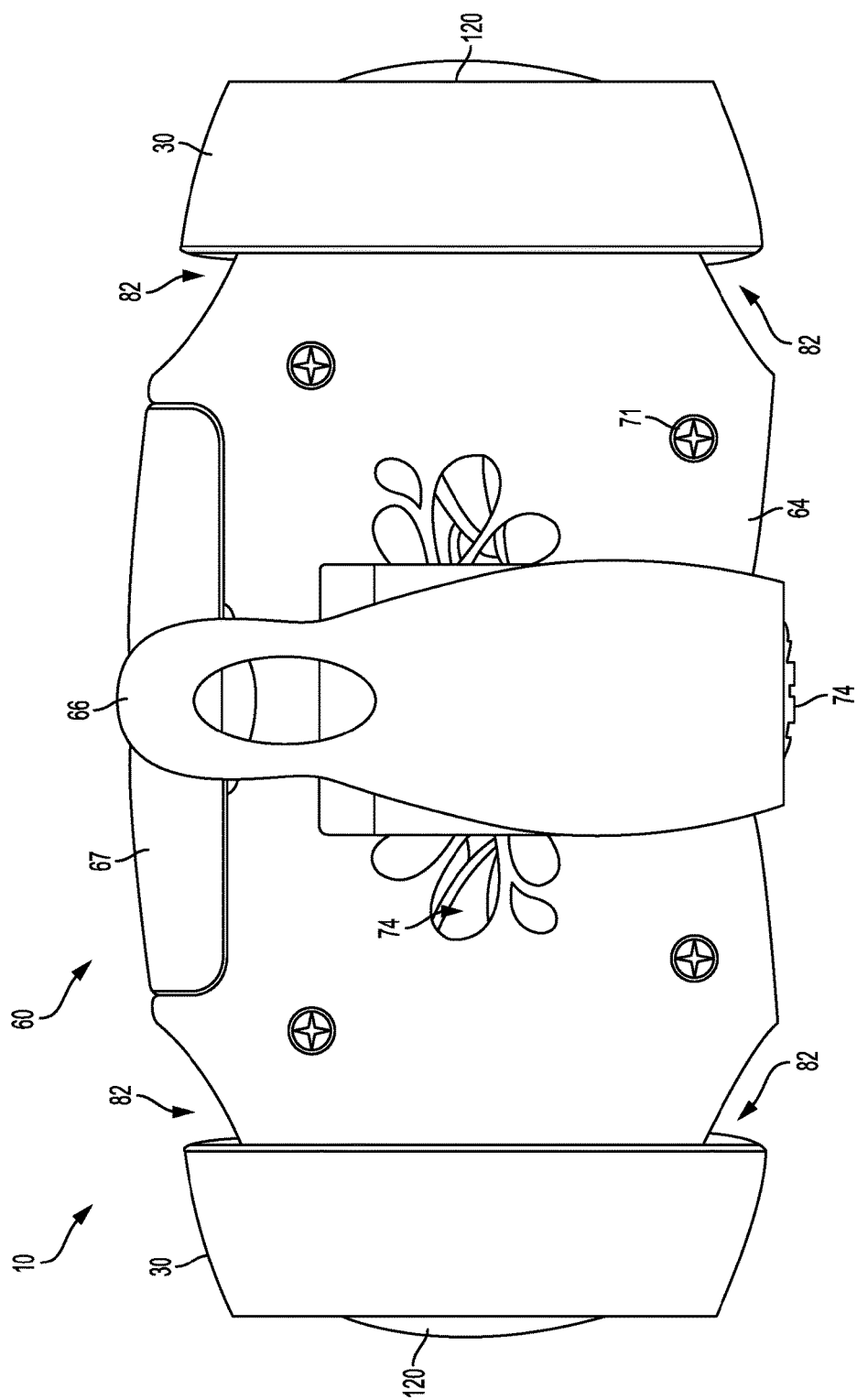
FIG. 21 is a side view of two diffusers having scent devices therein being carried by a panel-mount carrier, in accordance with an example embodiment.
Figure 22:
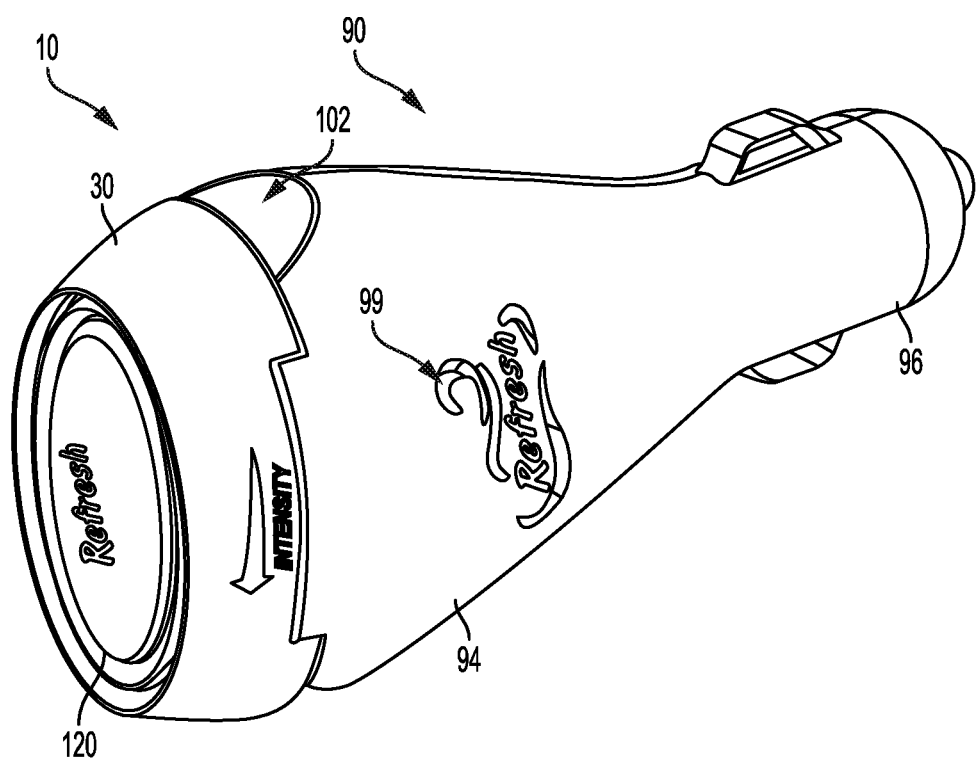
FIG. 22 is a perspective view of a diffuser having a scent device therein being carried by a plug in carrier, in accordance with an example embodiment.
Figure 23:
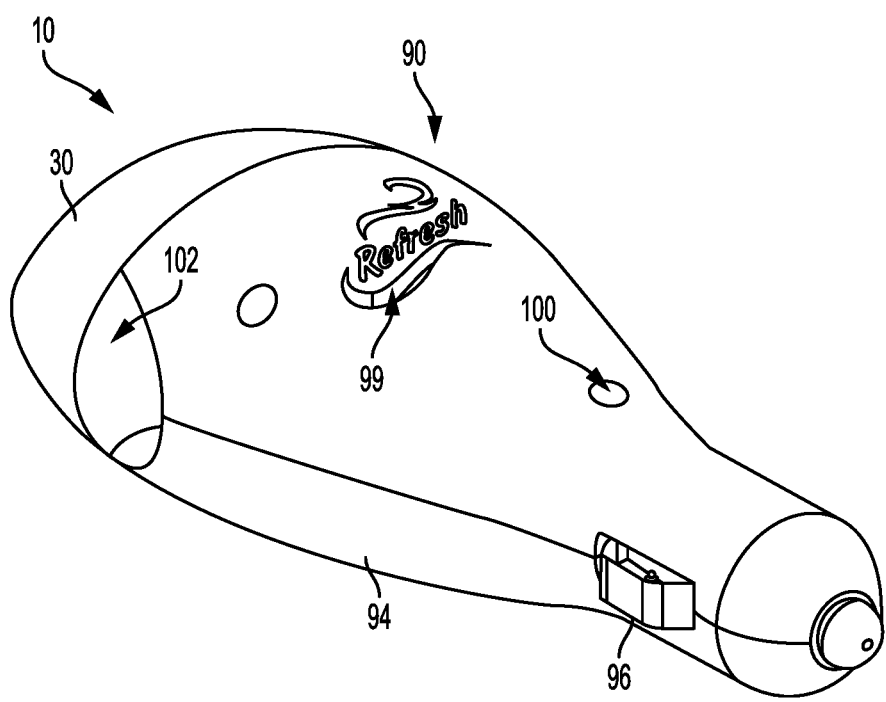
FIG. 23 is another perspective view of a diffuser having a scent device therein being carried by a plug in carrier, in accordance with an example embodiment.
Figure 24:
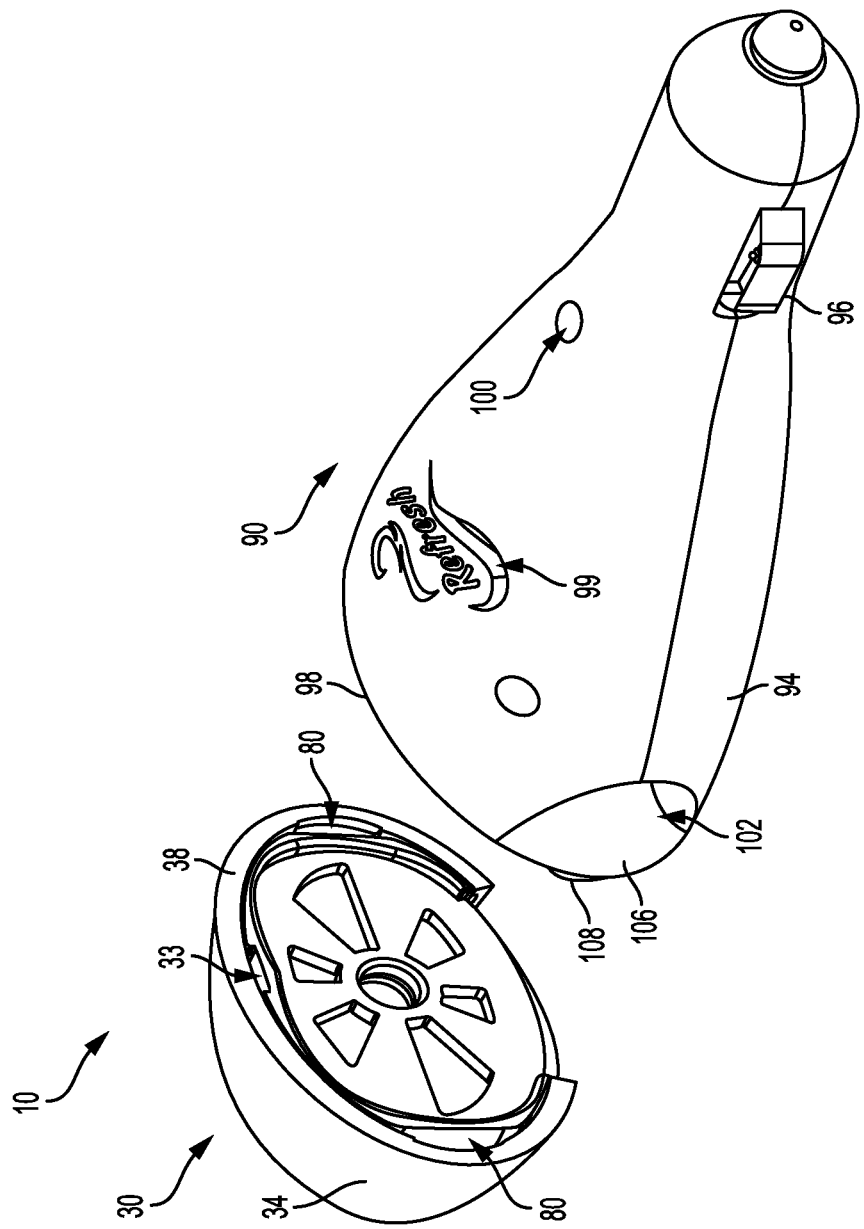
FIG. 24 is a partially exploded view of a diffuser having a scent device therein being carried by a plug in carrier, in accordance with an example embodiment.
Figure 25:
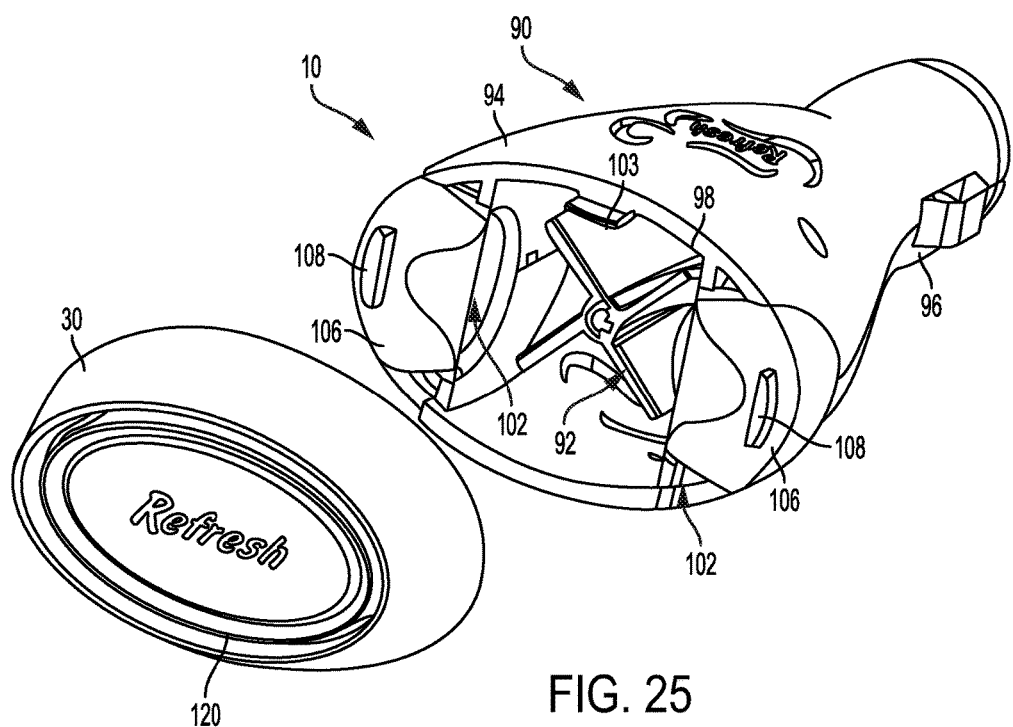
FIG. 25 is another partially exploded view of a diffuser having a scent device therein being carried by a plug in carrier, in accordance with an example embodiment.
Figure 26:
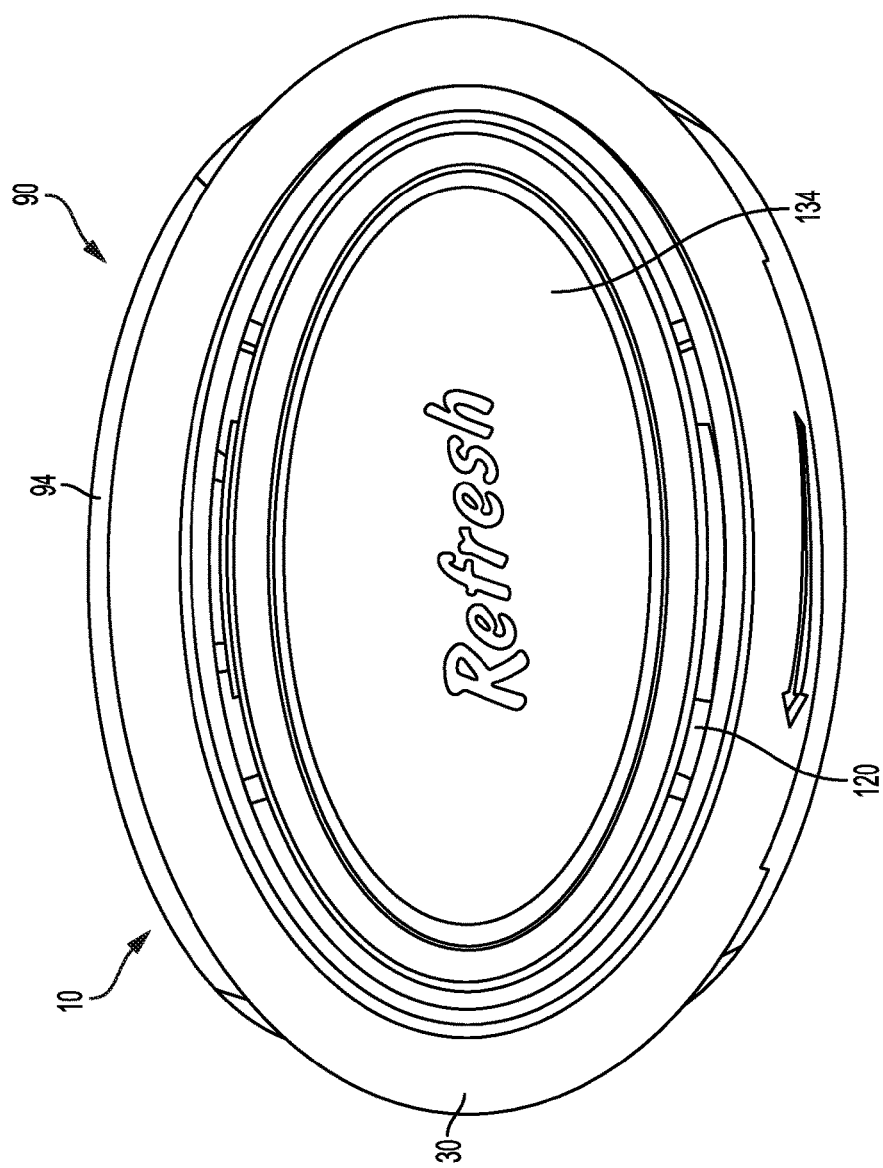
FIG. 26 is a front view of a diffuser having a scent device therein being carried by a plug in carrier, in accordance with an example embodiment.
Figure 28:
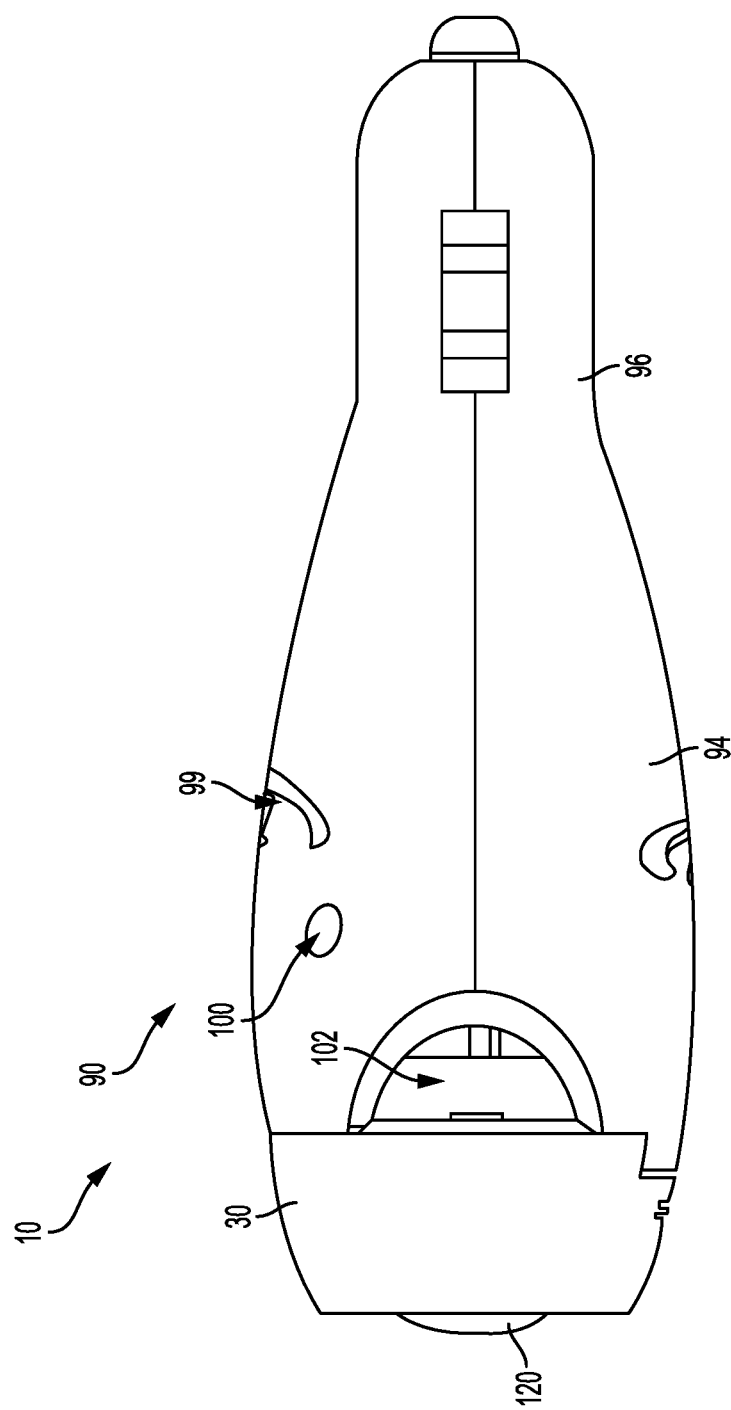
FIG. 28 is a side view of a diffuser having a scent device therein being carried by a plug in carrier, in accordance with an example embodiment.

As illustrated in the FIGS. 1-5, 7-10, 13-26, and 28, a modular air freshener system, indicated generally at 10, in an example implementation in accordance with the disclosure is shown for providing a scent or fragrance, particularly in a vehicle. The system 10 may include one or more of carriers 30, 60, 90 for scent devices or scent cartridges 120. In one embodiment, the scent cartridges are replaceable. The carriers may be one or more of a diffuser carrier 30 configured to be removably attachable to louvers of an air vent for example in a vehicle, a panel-clip carrier 60 configured to be removably attachable to a flat thin surface or panel, such as a visor of the vehicle, a plug-in carrier 90 configured to be powered and/or removably inserted at least partially into a power socket (e.g., cigarette type, USB, polarized plug, and/or the like) in the vehicle, and combinations thereof. The carriers can be passive, and may be configured to enable diffusion of the scented material therethrough. For example, the air displacement through the air vent in the vehicle (or building) may encourage diffusion of the scented material through the passive carrier engaged with a louver of the air vent. The carriers can be active, and can provide their own air displacement. The carriers can be self-powered, or externally powered by the vehicle electrical system. In addition, the body of one carrier can be a stand-alone carrier, and can complete the body or housing of another air freshener carrier. For example, the diffuser carrier 30 can be utilized in a stand-alone mode, by itself, or it can be affixed to the body or housing of the panel-mounted carrier 60 or plug-in carrier 90. Thus, the modular air freshener system 10 provides versatility and customization as desired by a user.

The modular air freshener system 10 comprises a plurality of different carriers (e.g., 30, 60, 90). The plurality of different carriers can include at least one self-powered carrier, at least one externally-powered carrier, and/or at least one unpowered or passive carrier. In example embodiments, the plurality of different carriers can be one or more of at least one visor-mounted carrier, at least one plug-in carrier, and/or at least one diffuser carrier or vent-mounted carrier. In one aspect, each of the plurality of carriers may be one of an unpowered or passive carrier, a vent-mount diffuser carrier 30; an active, self-powered, panel-mount carrier 60; and an active, externally-powered, plug-in carrier 90. In addition, the system comprises at least one scent device or cartridge 120. The scent device or cartridge 120 can be separately and removably carriable by each of the plurality of different carriers. Furthermore, at least one of the different carriers can be carriable by another one of the plurality of different carriers. In one aspect, the diffuser carrier 30 or portion thereof can be coupled to and carried by and incorporated into the panel-mount carrier 60 or the plug-in carrier 90. Furthermore, the body of one of the carriers can couple to and complete the body of another one of the carriers. For example the diffuser body 34 may couple to the panel-mount carrier body 64 and/or the plug-in carrier body 94.

The scent device 120 can have a scent. In one aspect, this scent device may have a scent material or fragrant material disposed therein. In example embodiments, the scent material or fragrant material may be and/or include a scented oil. This scent material can be held in a container or vessel closed by a permeable membrane. The container or vessel can include a sheet of plastic with an indentation surrounded by a flange. The permeable membrane can extend across the indentation and be affixed to the flange. A volume can be defined between the indentation and the permeable membrane and in which the scent material is disposed. The scent material can permeate the permeable membrane over time. In one aspect the container or vessel or sheet of plastic can be at the least translucent, or transparent, so the scent material can be viewed through the container or vessel or plastic sheet. The container or vessel or plastic sheet can form or define a dome 134 opposite the indentation. A release liner can extend across the permeable membrane and can be adhered around the perimeter of the membrane and the flange to seal the scent material in the vessel. The release liner can be removed by the user to release the scent. The scent device or cartridge 120, with the container or vessel closed by the permeable membrane, can be disposed in and carried by the body defining a cartridge or scent device 120. In example embodiments, the scent device or cartridge 120 may be similar to the scent capsules described in U.S. Pat. No. 8,673,223 and U.S. Pat. No. 9,042,712, the contents of which are hereby incorporated by reference in their entities.

The scent device or cartridge 120 can have a chamber containing a fragrant and/or scented material or liquid, and can have a substantially flat permeable membrane through which a fragrance of the fragrant material can permeate over time. The fragrant material can be a liquid, such as a fragrant oil. A scented liquid, such as oil, can be colored so that it is translucent to aid in visibility. The liquid or oil can also move in the chamber or vessel to aid in visibility. The permeable membrane can be located adjacent a blower that may comprise an impeller (e.g., 72, 92) and/or a vent (e.g., 82, 102). The membrane can be in close proximity to, and directly in front of, the blower (e.g., the impeller and/or vent). The permeable membrane can be substantially flat and oriented transverse, such as perpendicularly, to an axis of the motor 73, 93 and/or impeller 72, 92.

Figure 6:
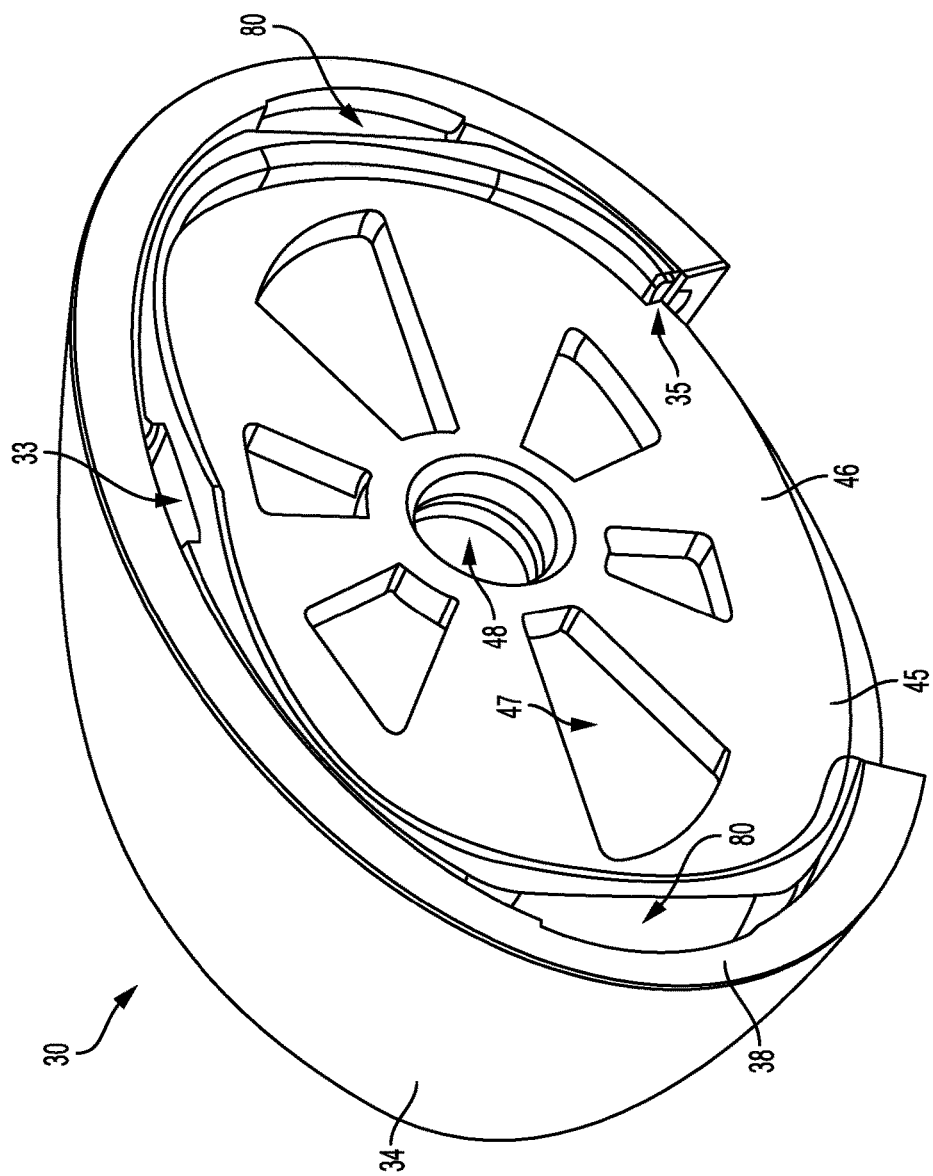
FIG. 6 is a perspective view of a portion of a diffuser, in accordance with an example embodiment.

Each of the carriers can comprise a housing or body. In example embodiments, the housing or body is formed by injection molding a plastic material. Each of the plurality of different carriers can have a different housing. As shown in FIGS. 1-9, the diffuser carrier 30 has a diffuser body 34 with a mating end 38. The diffuser body 34 can be annular with open ends 38 and 42. An outside or outer opening 42 can be smaller than an opposite interior opening 38. The scent device 120, such as the cartridge, can be inserted into the diffuser body 34 from the inside opening. The scent device or cartridge can be retained in the diffuser body 34 by retention plate 46. The retention plate 46 and the scent device or cartridge 120 can be removably disposed in the diffuser body 34. The mating end 38 may further comprise an alignment notch 33 and/or notches 80 for aiding in mounting the diffuser body 34 to a carrier body (e.g., 64, 94).

The dome 134 of the scent device or cartridge 120 can be disposed in the outer or exterior opening 42 of the diffuser body 34. The retention plate 46 can have a plurality of openings 47 that are selectively openable and closable by a pivot plate 50 pivotally coupled to the retention plate 46. For example, the pivot plate 50 may be rotated with respect to the retention plate 46 to adjust the degree of alignment between the retention plate openings 47 and the pivot plate openings 51 to control the intensity with which scent is released.

A mount or clip 54 can be removably coupled to the retention plate 46, and thus the diffuser body 34. A bore 48 can extend through the retention plate 46 and the pivot plate 50. The clip 54 can be removably inserted into the bore 48. The clip can include a bifurcated axle 56 that can be compressed and inserted into the bore 48. A pair of arms 58 can extend from the bifurcated axle 56 to engage a louver of an air vent of the vehicle, and releasably couple the diffuser to the air vent.

A tab 52 can extend from the pivot plate 50 out a lateral side of the diffuser body 34 so that a user can pivot the pivot plate with respect to the retention plate 46 to selectively align and misalign the openings 47 in the retention plate 46 and the openings 51 in the pivot plate 50 to increase or decrease, respectively, the release of scent. The scent device or cartridge 120 or dome 134 thereof can be smaller than the diffuser body 34 or hollow therein to define an annular gap between the scent device or cartridge 120 and the diffuser body 34 through which air can pass from the interior opening to the outer opening. In one aspect indicia 136 can be formed on the dome 134 of the scent device or cartridge 120. In one aspect the retention plate 46 can have a perimeter flange 45 that can snap fit into an interior annular groove 35 of the diffuser body 34. In another aspect, tabs on the pivot plate 50 can snap fit into the central bore 48 of the retention plate 46.

Figure 11:
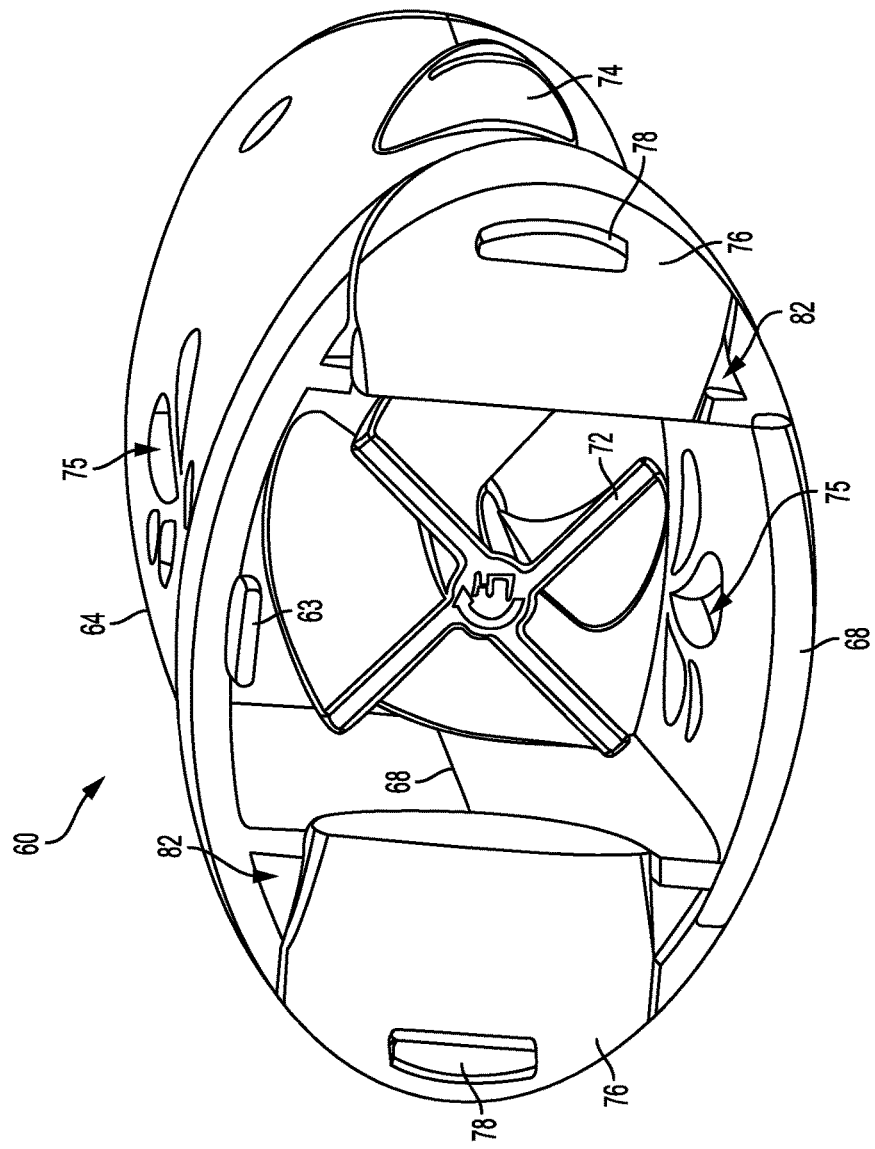
FIG. 11 is a perspective view of a panel-mount carrier, in accordance with an example embodiment.
Figure 12:
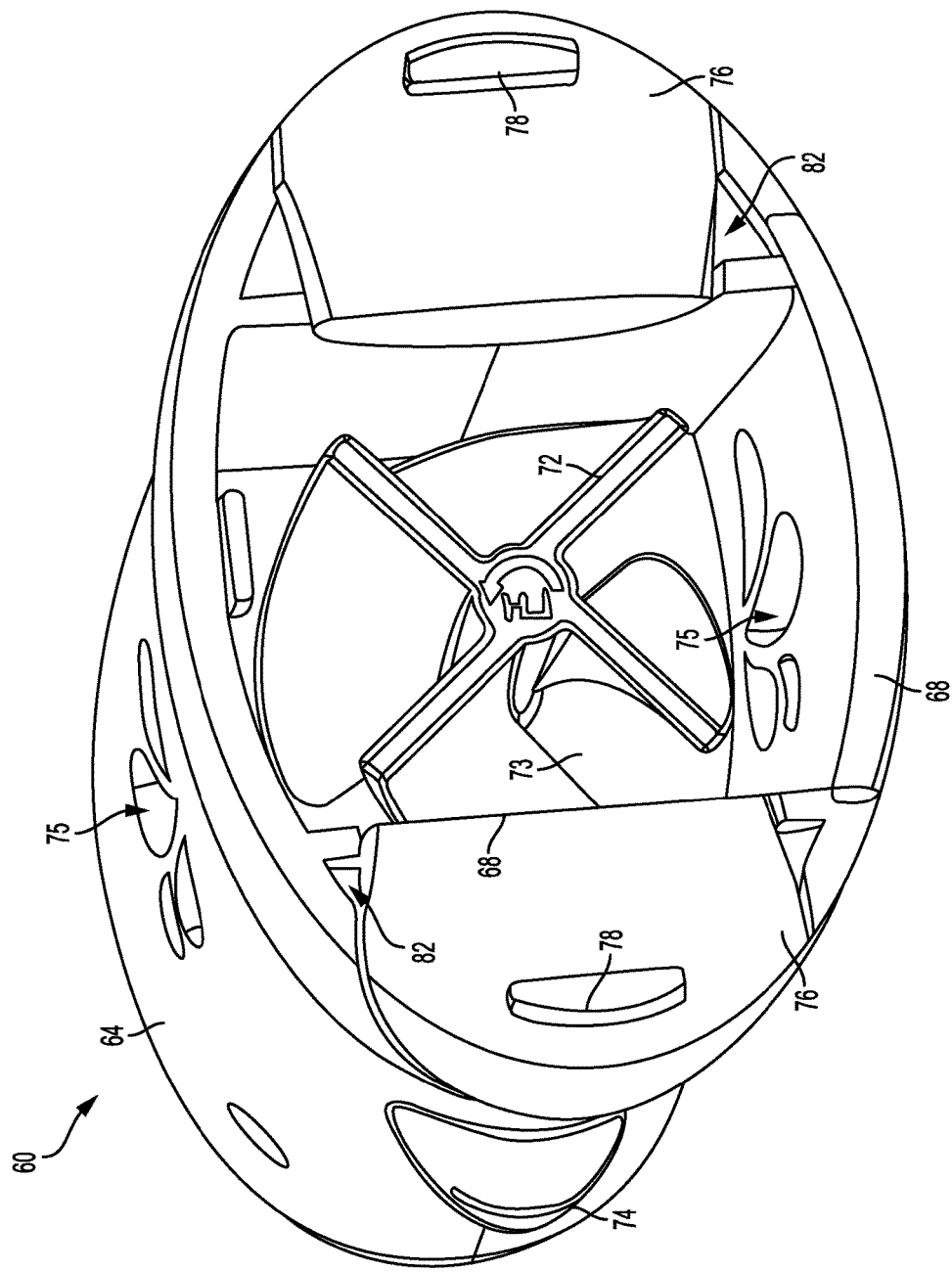
FIG. 12 is another perspective view of a panel-mount carrier, in accordance with an example embodiment.

In the illustrated embodiment of FIGS. 10-21, the panel-mount carrier 60 comprises a housing 64 and a clip 66 configured to clip the housing to a thin flat panel (e.g., a visor) with the panel between the housing and the clip, or between two portions of the clip. The clip 66 may be configured to removably attach the panel-mount carrier 60 to an object (e.g., a panel) that is generally flat and thin, such as a vehicle visor. The clip 66 may be secured to the housing 64 by inserting a clip tab 65 into the clip slot 69 such that the clip tab 65 is secured within the clip slot 69. The panel-mount housing 64 can be an elongated tubular housing with opposite open ends 68. The open ends 68 may each be configured to receive a diffuser body, thereby removably coupling a scent device or cartridge 120 to the housing 64. A battery can be disposed in a battery compartment within the housing that is selectively accessible by removing the battery compartment cover 67. A blower comprising an impeller 72 and a motor 73 can be disposed in the housing 64 with the battery electrically coupled to the motor 73. In one aspect, a plurality of blowers (e.g., collectively comprising a pair of impellers 72) can be disposed in the housing 64, each one disposed adjacent a different open end 68 of the panel-mount housing 64. In an example embodiment, the pair of impellers 72 can be driven by a single motor 73. A switch 74 can be disposed on the housing 64 and coupled to the battery for turning the motor 73 on and/or off. The mating end 38 of the diffuser body 34 can be selectively couplable to the open end 68 of the housing 64 of the panel-mount carrier 60 to complete the housing of the panel-mount carrier 60. Thus, the scent device 120 or cartridge is positioned proximate the impeller 72, with the panel-mount carrier 60 carrying the diffuser body 34 and the scent device 120.

In an example embodiment, the housing 65 may comprise air vents 75 to allow air to flow into and/or out of the interior of the housing 64, for example, when the blowers (e.g., comprising impeller(s) 72) are activated to increase the dispersal of scent from the scent device or cartridge 120. The housing 65 may further comprise fastener holes 77. For example, the housing 64 may comprise two housing halves that are secured together by fasteners 71 through the fastener holes 77 once the motor 73 and impeller(s) 72 have been mounted within the housing 64. In one example embodiment, securing the two housing halves together by fasteners 71 may mount the motor 73 and impeller(s) 72 within the housing 64.

In one aspect, the housing 64 of the panel-mount carrier 60 can have a pair of opposite flexible fingers 76 disposed at opposite ends of the open end 68. The pair of flexible fingers can engage the diffuser body 34, or mounting end 38 thereof. Each of the flexible fingers can have a tab 78 that engages a notch 80 in the diffuser body 34. Thus, to attach the diffuser body to the housing 64 of the panel-mount carrier 60, a user can squeeze the pair of fingers 76 together so that the tabs 78 move together and can be received in the mounting end 38 or interior opening of the diffuser body 34 (e.g., in the notches 80). The pair of fingers 76 can be biased outwardly so that the tabs 78 engage the notches 80 in the diffuser body 34. To release the diffuser body 34, the user can pinch the pair of fingers 76 and remove the diffuser body 34. In an example embodiment, the open end 68 may further comprise an alignment projection 63 that may be inserted into the alignment notch 33 when the diffuser body 34 is carried by the panel-mount carrier 60.

In one aspect, the body 34 of the diffuser carrier 30 can be flush with the housing 64 of the panel-mount carrier 60. The diffuser body 34 can be removably couplable to the housing 64 of the panel-mount carrier 60. Thus, the scent device or cartridge 120 disposed in and carried by the body 34 of the diffuser carrier 30 is removably couplable to the housing 64 along with the diffuser body 34. A pair of notches or vents 82 for scent distribution can be formed in the housing 64 of the panel-mount carrier 60 adjacent to the pair of fingers 76.

Figure 27:
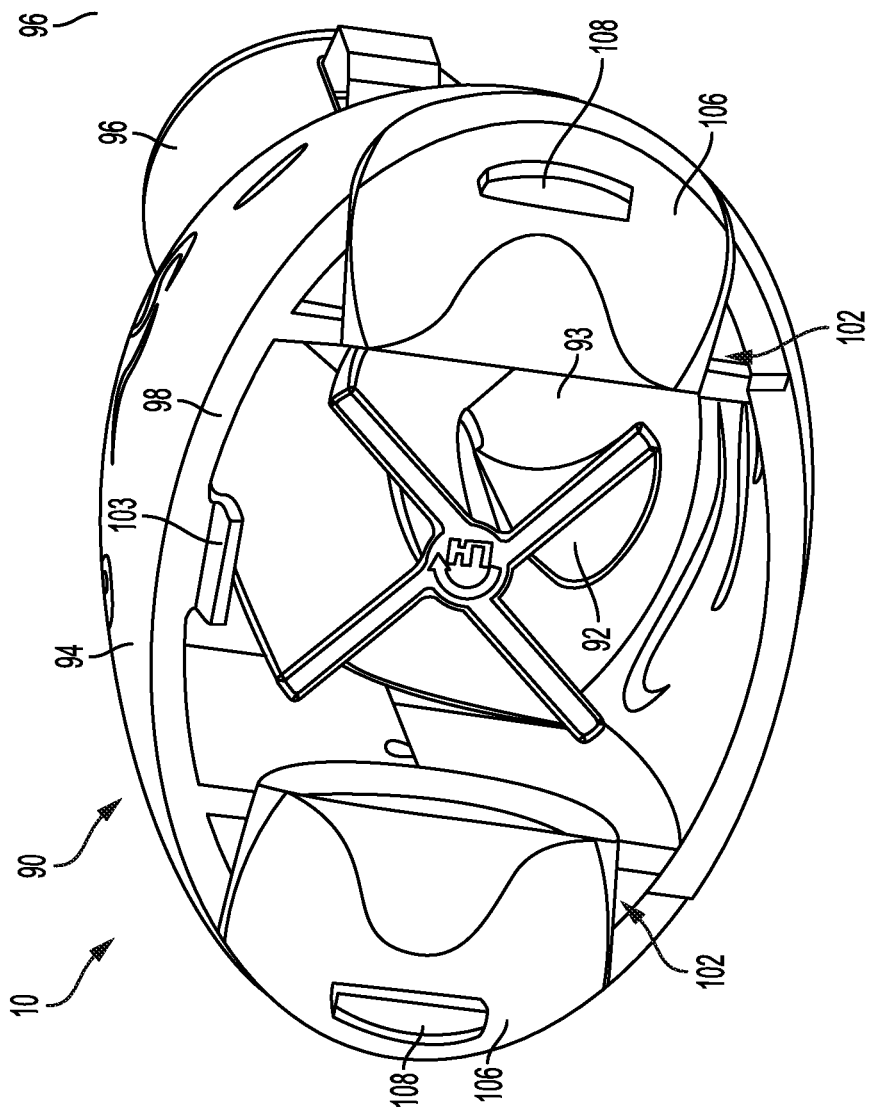
FIG. 27 is a perspective view of a plug in carrier, in accordance with an example embodiment.

As shown in FIGS. 22-28, the plug-in carrier 90 comprises a housing 94 having a portion (such as a stem 96) sized and shaped to be inserted into a power socket, such as a 12 volt DC power outlet of a vehicle, a 110 volt AC power outlet of a home, a USB receptacle, and/or the like. For example, such an outlet is a power outlet for an accessory or cigarette lighter, and is often located in a dash or console of a vehicle. The plug-in carrier 90 can use power from the vehicle to power a blower (e.g., comprising motor 93 and impeller 92 (and/or a heat source configured to heat the scent material)) to accelerate dispersion of a fragrance, etc. The stem 96 can be removably coupled to the outlet so that the plug-in carrier can be inserted as a retrofit accessory, and withdrawn as desired. The stem 96 is sized and shaped to be inserted into the power outlet, such as a 12 volt outlet, of the automobile, and includes a pair of terminals or electrical contacts thereon capable of contacting mating terminals in the power outlet. The pair of terminals can include a bottom tip or distal end terminal and one or more lateral side terminals, corresponding to a bottom terminal and one or more lateral terminals in the power outlet, respectively. For example, the stem may comprise terminals similar to those described in U.S. Pat. No. 8,662,480, the contents of which are hereby incorporated by reference in their entireties. In example embodiments, the stem 96 of the plug-in carrier 90 may comprise a USB plug or polarized plug such that the plug-in carrier may be powered through a USB receptacle or a polarized outlet, respectively. A blower, which may comprise an impeller 92 and a motor 93 can be disposed in the housing 94 with the motor 93 electrically coupled to the terminals. An open end 98 is formed in the housing 94 with the impeller 92 adjacent the open end 98. The open end 98 may be configured to receive a diffuser body 34, thereby removably coupling a scent device or cartridge 120 to the housing 94. For example, the mating end 38 of the diffuser body 34 can be selectively couplable to the open end 98 of the housing 94 of the plug-in carrier 90 to complete the housing 94 of the plug-in carrier 90. Thus, the scent device or cartridge 120 is positioned proximate the impeller 92, with the plug-in carrier 90 carrying the diffuser body 34 and the scent device 120.

In an example embodiment, the housing 94 may comprise air vents 99 to allow air to flow into and/or out of the interior of the housing 94, for example, when the impeller 92 and/or heater are activated to increase the dispersal of scent from the scent device or cartridge 120. The housing 94 may further comprise fastener holes 100. For example, the housing 94 may comprise two housing halves that are secured together by fasteners through the fastener holes 100 once the blower (e.g., motor 93 and impeller 92) and/or heater have been mounted within the housing 94. In an example embodiment, securing the two housing halves with the fasteners may act to mount the motor 93 and impeller 92 and/or heater within the housing 94.

In one aspect, the housing 94 of the plug-in carrier 90 can have a pair of opposite flexible fingers 106 disposed at opposite ends of the open end 98. The pair of flexible fingers 106 can engage the diffuser body 34, or mounting end 38 thereof. Each of the flexible fingers can have a tab 108 that engages in a notch 80 in the diffuser body 34. Thus, to attach the diffuser body 34 to the housing 94 of the plug-in carrier 90, a user can squeeze the pair of fingers 106 together so that the tabs 108 move together and can be received in the mounting end 38 or interior opening of the diffuser body 34. The pair of fingers 106 can be biased outwardly so that the tabs 108 engage the notches 80 in the diffuser body 34. To release the diffuser body 34, the user can pinch the pair of fingers 106 and remove the diffuser body 34. In an example embodiment, the open end 98 may further comprise an alignment projection 103 that may be inserted into the alignment notch 33 when the diffuser body 34 is carried by the panel-mount carrier 60.

In one aspect, the body 34 of the diffuser carrier 30 can be flush with the housing 94 of the plug-in carrier 90. The diffuser body 34 can be removably couplable to the housing 94 of the carrier 90. Thus, the scent device or cartridge 120 disposed in and carried by the body 34 of the diffuser carrier 30 is removably couplable to the housing 94 along with the diffuser body 34. A pair of notches or vents 82 for scent distribution can be formed in the housing 94 of the plug-in carrier 90 adjacent to the pair of fingers 106. The body of one of the carriers (such as the diffuser carrier 30) couples to and completes a body or housing of another one of the carriers (such as the panel-mount carrier 60 or the plug-in carrier 90). The mating or interior open end 38 of the diffuser body 34 can abut to the open end 68, 98 of the housing 64, 94 of the panel-mount carrier 60 or the plug-in carrier 90.

The clip or mount 54 can be couplable to the diffuser body 34 when the diffuser body is removed from the housing of either of the panel-mount carrier 60 or the plug-in carrier 90. The clip or mount 54 can comprise a vent clip with a pair of arms 58 configured to be inserted into the air vent and engage a louver of the air vent.

As described above, at least one scent device or cartridge 120 can be separately and removably carriable by each of the plurality of different carriers (diffuser carrier 30, panel-mount carrier 60, and plug-in carrier 90). Also as described above, at least one of the different carriers (such as a diffuser carrier 30) can be carriable by another one of the plurality of different carriers (such as the panel-mount carrier 60 or the plug-in carrier 90).

A blower is one example of a scent distributor for accelerating dispersal of scent disposed in the scent device or cartridge 120. In example embodiments, the blower is configured to supply a flow of air through the open end 68, 98 of a housing 64, 94 of self-powered or externally-powered carrier 60, 90. In an example embodiment, the blower may comprise one or more impellers 72, 92 and a motor 73, 93 for operating the one or more impellers. A heat source configured to heat the scent material is another example of a scent distributor for accelerating dispersal of scent disposed in the scent device or cartridge 120.

The housing of the carrier 60, 90, the diffuser body 34, the scent distributor, and the scent device 120 can define an active air freshener when the diffuser body 34 and the scent device 120 is coupled to the housing 64, 94, with the diffuser body 34 carried by the housing 64, 94 and the scent distributor accelerating dispersal of scent from the scent device 120. The diffuser body 34, the scent device 120 and the mount (e.g., clip 54) can define a passive air freshener when the diffuser body 34 and the scent device 120 are removed from the housing 64, 94 and the mount (e.g., clip 54) is coupled to the diffuser body 34, with the diffuser body 34 carried by the mount (e.g., clip 54).

Many modifications and other embodiments of the disclosure set forth herein will come to mind to one skilled in the art to which the disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A modular air freshener system, the system comprising:
a plurality of carriers each carrier having a different housing, the plurality of carriers comprising a passive diffuser carrier; a self-powered carrier; and an externally-powered carrier;
the self-powered carrier comprising:
a first housing defining a first open end;
a power-supply disposed in the first housing; and
a first blower electrically connected to the power supply, wherein the first blower is disposed in the first housing and configured to supply a flow of air through the first open end;
the externally-powered carrier comprising:
a second housing comprising at least one electrical terminal configured to be secured relative to an external power supply, wherein the second housing defines a second open end; and
a second blower electrically connected to the at least one electrical terminal, wherein the second blower is disposed in the second housing and configured to supply a flow of air through the second open end; and
the passive diffuser carrier comprising:
a diffuser body having a mating end; and
a scent device carried at least partially in the diffuser body;
wherein the mating end of the diffuser body is selectively couplable to the first open end of the first housing to complete the first housing of the self-powered carrier, and to position the scent device in the air flow provided by the first blower, the self-powered carrier carrying the diffuser body and the scent device;
wherein the mating end of the diffuser body is selectively couplable to the second open end of the second housing of the externally-powered carrier to complete the second housing of the externally-powered carrier, and to position the scent device in the flow path of the second blower, the externally-powered carrier carrying the diffuser body and the scent device; and
a mount couplable to the diffuser body when the diffuser body is not coupled to the first housing and the second housing;
the mount comprising a vent clip configured to be removably attachable to an air vent.

2. The modular air freshener system of claim 1, wherein the at least one electrical terminal comprises a distal end terminal and at least one lateral side terminal.

3. The modular air freshener system of claim 1, wherein the first housing of the self-powered carrier further comprises a third open end formed in the first housing and configured to have a second diffuser body selectively coupled thereto.

4. The modular air freshener system of claim 3, wherein the first blower comprises a first impeller, a second impeller, and a motor, wherein the first impeller is disposed adjacent the first open end and the second impeller is disposed adjacent the third open end, wherein the first impeller and the second impeller are operated by the motor, wherein, the motor is electrically connected to the power supply.

5. An air freshener system, comprising:
an active air freshener comprising:
a housing;
a diffuser body configured to be coupled to the housing;
a scent device disposed in and carried by the diffuser body; and
a scent distributor for accelerating dispersal of scent material disposed in the scent device; and
a passive air freshener comprising:
the diffuser body having the scent device disposed and carried therein; and a mount configured to be coupled to the diffuser body and carrying the diffuser body.

6. The system in accordance with claim 5, wherein the scent distributor comprises a blower disposed in the housing and configured to supply a flow of air.

7. The system in accordance with claim 5, wherein the scent distributor comprises a heater disposed within the housing and configured to heat the scent material disposed within the scent device.

8. The system in accordance with claim 5, wherein the active air freshener is externally-powered; and wherein the housing comprises a stem portion sized and shaped to be inserted into a power outlet.

9. The system in accordance with claim 5, wherein the active air freshener is self-powered; and the housing comprises a battery compartment configured for housing a battery therein such that the battery is electrically coupled to the scent distributor.

10. The system in accordance with claim 5, wherein the passive air freshener is configured to position the scent device proximal an air vent of a vehicle; and wherein the mount comprises a vent clip with a pair of arms configured to be inserted into the air vent and engage a louver of the air vent.

11. The system in accordance with claim 5, wherein the housing comprises a pair of flexible fingers, each flexible finger comprising a tab configured to removably couple with a notch disposed on the diffuser body.

12. The system in accordance with claim 5, further comprising:
a second diffuser body; and
a second scent device disposed in and carried by the second diffuser body and being removably couplable to the housing along with the second diffuser body,
wherein the housing is configured to receive both the diffuser body and the second diffuser body such that both the diffuser body and the second diffuser body are removably coupled to the housing.

13. The system in accordance with claim 12, further comprising a second scent distributor.

14. The system in accordance with claim 13, wherein the scent distributor comprises a motor and a first impeller and the second scent distributor comprises a second impeller, wherein the first impeller is positioned proximate the scent device and the second impeller is positioned proximate the second scent device, and wherein the first and second impeller are operated by the motor.

15. The system in accordance with claim 5, wherein the diffuser body comprises a retention plate configured to removably retain the scent device within the diffuser body and comprising a plurality of openings configured for the dispersal of the scent material therethrough.

16. The system in accordance with claim 15, wherein the diffuser body further comprises a pivot plate configured to rotate with respect to the retention plate and comprising a plurality of openings, wherein the pivot plate may be rotated with respect to the retention plate to adjust the degree of alignment between the retention plate openings and the pivot plate openings to control the intensity with which the scent material is released.

17. The system in accordance with claim 5, wherein the housing comprises:
at least one open end configured to receive the diffuser body; and
one or more scent dispersal vents located proximate the open end.

18. A diffuser body, the diffuser body comprising:
an opening for receiving a scent device therein;
at least one first coupling element for coupling a mount to the diffuser body for use of the diffuser body as a passive air freshener; and
one or more one second coupling elements for coupling the diffuser body to a housing for use of the diffuser body coupled to the housing as an active air freshener.

19. The diffuser body in accordance with claim 18, wherein the one or more second coupling element comprises an alignment element and an engaging element.

20. The diffuser body in accordance with claim 18, further comprising a retention plate comprising one or more plate openings and configured to maintain the scent device within the opening.

* * * * *